US012690926B2

(12) United States Patent
Adebar et al.

(10) Patent No.: US 12,690,926 B2
(45) Date of Patent: Jul. 28, 2026

(54) SYSTEMS FOR DYNAMIC IMAGE-BASED LOCALIZATION AND ASSOCIATED METHODS

(71) Applicant: INTUITIVE SURGICAL OPERATIONS, INC., Sunnyvale, CA (US)

(72) Inventors: Troy K. Adebar, San Jose, CA (US); Timothy D. Soper, San Jose, CA (US); Kevin X. Pluckter, Santa Clara, CA (US)

(73) Assignee: INTUITIVE SURGICAL OPERATIONS, INC., Sunnyvale, CA (US)

( * ) Notice: Subject to any disclaimer, the term of this patent is extended or adjusted under 35 U.S.C. 154(b) by 175 days.

(21) Appl. No.: 18/260,307

(22) PCT Filed: Dec. 27, 2021

(86) PCT No.: PCT/US2021/065205
§ 371 (c)(1),
(2) Date: Jul. 3, 2023

(87) PCT Pub. No.: WO2022/146918
PCT Pub. Date: Jul. 7, 2022

(65) Prior Publication Data
US 2024/0050160 A1 Feb. 15, 2024

Related U.S. Application Data

(60) Provisional application No. 63/133,743, filed on Jan. 4, 2021.

(51) Int. Cl.
A61B 34/20 (2016.01)
A61B 34/10 (2016.01)
A61B 90/00 (2016.01)

(52) U.S. Cl.
CPC .............. *A61B 34/20* (2016.02); *A61B 34/10* (2016.02); *A61B 90/37* (2016.02); *A61B 2034/105* (2016.02); *A61B 2034/2065* (2016.02)

(58) Field of Classification Search
None
See application file for complete search history.

(56) References Cited

U.S. PATENT DOCUMENTS 6,389,187 B1 5/2002 Greenaway et al.
7,772,541 B2 8/2010 Froggatt et al.
(Continued)

OTHER PUBLICATIONS

International Preliminary Report on Patentability for Application No. PCT/US2021/065205 mailed Jul. 13, 2023, 10 pages.
(Continued)

*Primary Examiner* — Patricia J Park
(74) *Attorney, Agent, or Firm* — Haynes & Boone, LLP

(57) ABSTRACT

Devices, systems, methods, and computer program products for performing medical procedures are disclosed herein. In some embodiments, a system for performing a medical procedure includes a medical instrument configured to be inserted within the anatomic region, the medical instrument including an image capture device. The system can be configured to obtain, from the image capture device, image data of an anatomic landmark within the anatomic region. The system can identify, based on the image data, an association between the anatomic landmark and a corresponding model landmark in a model of the anatomic region. The system can determine a localization state of the medical instrument based on the identified association, the localization state including an estimated location and an uncertainty parameter associated with the estimated location. The system can dynamically update the localization state as the medical instrument navigates within the anatomic region.

20 Claims, 11 Drawing Sheets

100

110 — Receive a 3D model of an anatomic region

120 — Obtain image data of the anatomic region

130 — Determine a localization state of a medical instrument in the anatomic region 135 — Estimate a location of the medical instrument relative to an anatomic landmark 140 — Dynamically update the localization state 150 — Display a graphical representation of the localization state

(56) References Cited

U.S. PATENT DOCUMENTS

| | | | |
|---|---|---|---|
| 7,781,724 | B2 | 8/2010 | Childers et al. |
| 2005/0054900 | A1* | 3/2005 | Mawn ................... A61B 5/064 |
| | | | 600/156 |
| 2006/0013523 | A1 | 1/2006 | Childlers et al. |
| 2011/0087091 | A1* | 4/2011 | Olson ...................... A61B 8/08 |
| | | | 600/437 |
| 2015/0265368 | A1* | 9/2015 | Chopra ........... A61B 1/000094 |
| | | | 600/587 |
| 2018/0235709 | A1* | 8/2018 | Donhowe .............. A61B 34/35 |
| 2019/0365486 | A1* | 12/2019 | Srinivasan ............. A61B 34/20 |
| 2020/0046434 | A1 | 2/2020 | Graetzel et al. |
| 2020/0297444 | A1* | 9/2020 | Camarillo ............. G16H 30/40 |
| 2022/0071715 | A1 | 3/2022 | Donhowe et al. |
| 2022/0343504 | A1 | 10/2022 | Donhowe et al. |

OTHER PUBLICATIONS

International Search Report and Written Opinion for Application No. PCT/US2021/065205, mailed May 18, 2022, 17 pages.
Vertut, J, and Coiffet, P., "Robot Technology: Teleoperation and Robotics Evolution and Development," English translation, Prentice-Hall, Inc., Inglewood Cliffs, NJ, USA 1986, vol. 3A, 332 pages.

\* cited by examiner

100

110 —
Receive a 3D model of an anatomic region

120 —
Obtain image data of the anatomic region

130 —
Determine a localization state of a medical instrument in the anatomic region 135 —
Estimate a location of the medical instrument relative to an anatomic landmark 140 —
Dynamically update the localization state 150 —
Display a graphical representation of the localization state 400a
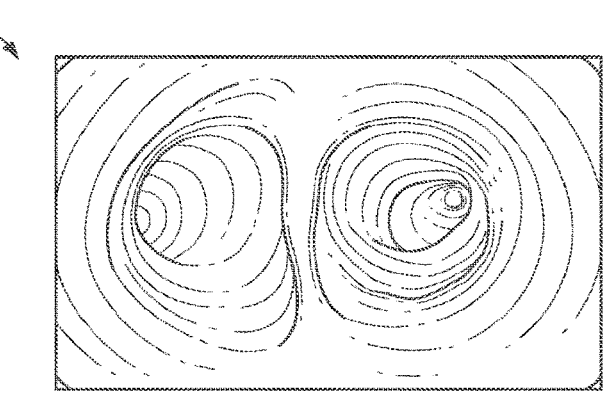
*FIG. 4A*
400b
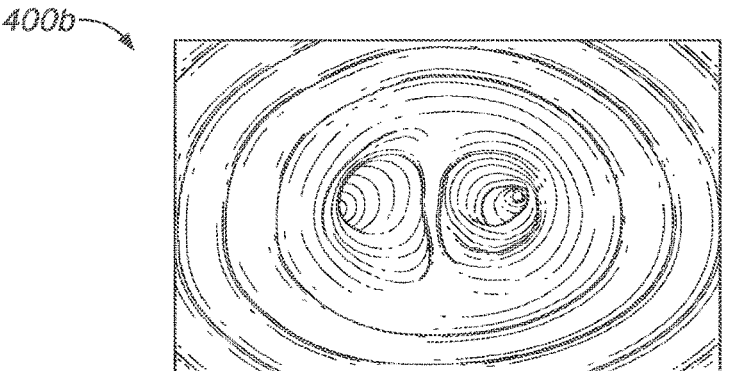
*FIG. 4B*
400c
400d
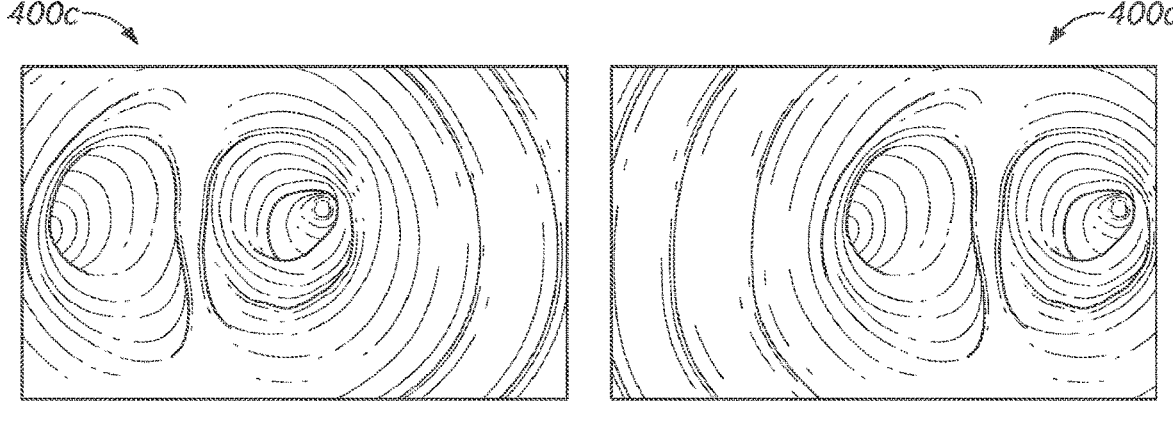
*FIG. 4C*       *FIG. 4D*

SYSTEMS FOR DYNAMIC IMAGE-BASED LOCALIZATION AND ASSOCIATED METHODS

CROSS-REFERENCE TO RELATED APPLICATIONS

This application is the U.S. National Stage patent application of International Patent Application No. PCT/US2021/065205 filed on Dec. 27, 2021, which claims the benefit of and priority to U.S. Provisional Application 63/133,743 filed Jan. 4, 2021, each of which is incorporated by reference herein in its entirety.

This application incorporates by reference in their entirety International Publication Number WO 2022/146911, titled "Image-Based Seeding for Registration and Associated Systems and Methods" and International Publication Number WO 2022/146919, titled "Systems for Image-Based Registration and Associated Methods."

TECHNICAL FIELD

The present disclosure is directed to systems, methods, and computer program products for monitoring a localization state of a medical instrument during a medical procedure.

BACKGROUND

Minimally invasive medical techniques are intended to reduce the amount of tissue that is damaged during medical procedures, thereby reducing patient recovery time, discomfort, and harmful side effects. Such minimally invasive techniques may be performed through natural orifices in a patient anatomy or through one or more surgical incisions. Through these natural orifices or incisions, an operator may insert minimally invasive medical tools to reach a target tissue location. Minimally invasive medical tools include instruments such as therapeutic, diagnostic, biopsy, and surgical instruments. Medical tools may be inserted into anatomic passageways and navigated toward a region of interest within a patient anatomy. Navigation may be assisted using images of the anatomic passageways. Improved systems and methods are needed to accurately perform registrations between medical tools and images of the anatomic passageways.

SUMMARY

Disclosed herein are devices, systems, methods, and computer program products for performing a medical procedure, including monitoring a localization state of medical instrument during the medical procedure. In some embodiments, a system for performing a medical procedure includes a medical instrument configured to be inserted within the anatomic region, the medical instrument including an image capture device. The system can also include a processor operably coupled to the image capture device, and a memory operably coupled to the processor. The memory can store instructions that, when executed by the processor, cause the system to perform operations including: receiving a three-dimensional (3D) model of the anatomic region; obtaining, from the image capture device, image data of an anatomic landmark within the anatomic region; and identifying, based on the image data, an association between the anatomic landmark and a corresponding model landmark in the 3D model. The operations can also include determining a localization state of the medical instrument based, at least in part, on the association between the anatomic landmark and the corresponding model landmark. The localization state can include an estimated location of the medical instrument and an uncertainty parameter associated with the estimated location. The operations can further include dynamically updating the localization state as the medical instrument traverses the anatomic region.

In these and other embodiments, a non-transitory, computer-readable medium can store instructions that, when executed by one or more processors of a computing system, cause the computing system to perform operations including: receiving a 3D model of an anatomic region; obtaining, from an image capture device carried by a medical instrument within the anatomic region, image data of an anatomic landmark within the anatomic region; and identifying, based on the image data, an association between the anatomic landmark and a corresponding model landmark in the 3D model. The operations can also include determining a localization state of the medical instrument based, at least in part, on the association between the anatomic landmark and the corresponding model landmark. The localization state can include an estimated location of the medical instrument and an uncertainty parameter associated with the estimated location. The operations can further include dynamically updating the localization state as the medical instrument traverses the anatomic region.

In these and still other embodiments, a method can include: receiving a 3D model of an anatomic region; obtaining, from an image capture device carried by a medical instrument within the anatomic region, image data of an anatomic landmark within the anatomic region; and identifying, based on the image data, an association between the anatomic landmark and a corresponding model landmark in the 3D model. The method can also include determining a localization state of the medical instrument based, at least in part, on the association between the anatomic landmark and the corresponding model landmark. The localization state can include an estimated location of the medical instrument and an uncertainty parameter associated with the estimated location. The method can further include dynamically updating the localization state as the medical instrument traverses the anatomic region.

BRIEF DESCRIPTION OF THE DRAWINGS

Many aspects of the present disclosure can be better understood with reference to the following drawings. The components in the drawings are not necessarily to scale. Instead, emphasis is placed on illustrating clearly the principles of the present disclosure. The drawings should not be taken to limit the disclosure to the specific embodiments depicted, but are for explanation and understanding only.

FIGS. 4A-4D illustrate a plurality of images obtained at the imaging locations of FIG. 3 in accordance with various embodiments of the present technology.

DETAILED DESCRIPTION

Figure 1:
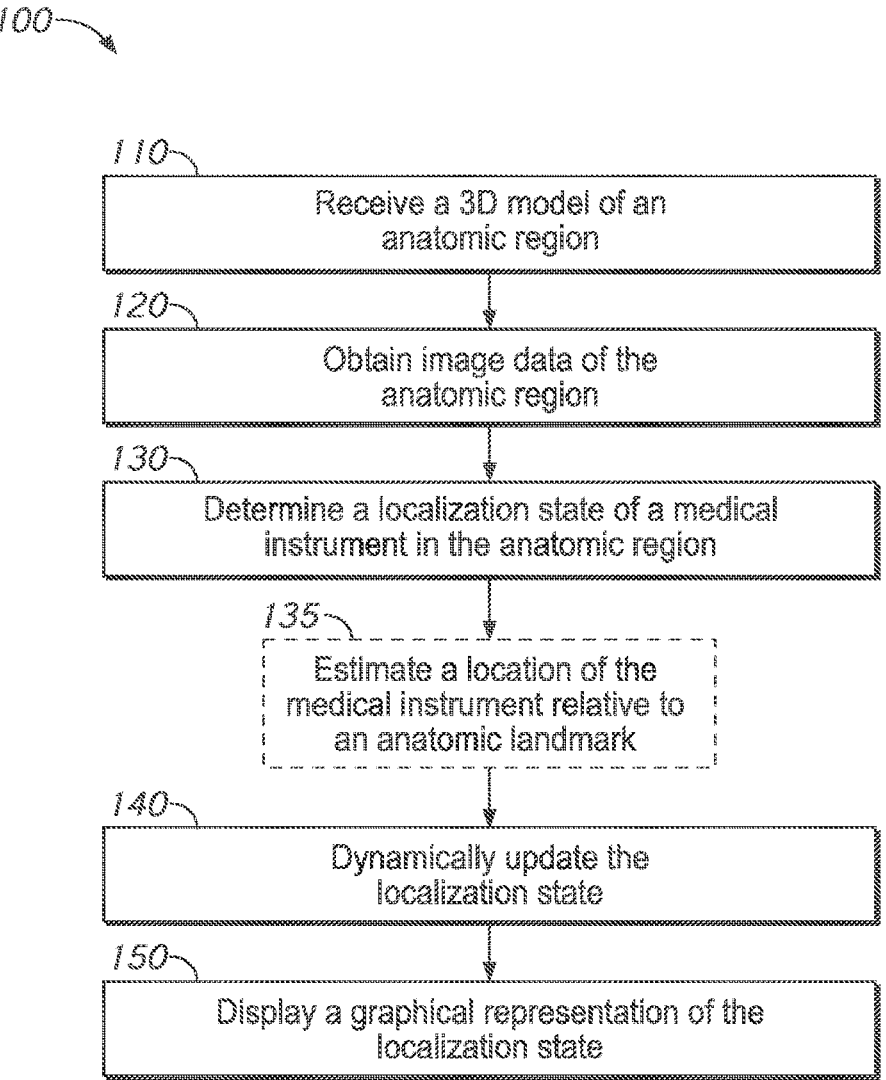
FIG. 1 is a flow diagram illustrating a method for monitoring a location of a medical instrument during a medical procedure in accordance with various embodiments of the present technology.

The present disclosure is directed to devices, systems, methods, and computer program products for monitoring a localization state of a medical instrument during a medical procedure in an anatomic region of a patient. In some embodiments, an image-guided medical procedure uses a 3D model of the anatomic region to assist an operator in navigating a medical device or instrument within the patient. The 3D model is typically mapped to the patient anatomy in an initial registration procedure so that the location of the instrument within the patient can be tracked to a corresponding location within the model. Accurate tracking of the medical instrument may be particularly important for procedures performed within complex, dense, and/or tortuous anatomic regions, such as the airways of the lungs. However, if the initial registration is not sufficiently accurate, the system may not be able to correctly map and track the location of the medical instrument. Moreover, the tracking may fail if the operator drives the medical instrument into portions of the anatomic region not covered by the 3D model and/or if the 3D model does not accurately represent the actual patient anatomy.

Accordingly, the systems disclosed herein can use image data to monitor and dynamically update the localization state of the medical instrument, in combination with or as an alternative to an initial registration. In some embodiments, for example, the systems disclosed herein are configured to obtain image data using an image capture device (e.g., an endoscopic camera) carried by a medical instrument within the anatomic region. The system can use the image data to determine the localization state of the medical instrument, such as an estimated location of the instrument and an uncertainty parameter for the estimated location. For example, the system can use image data to determine the location of the medical instrument relative to specific anatomic landmark(s) (e.g., carina(s)) in the anatomy. The localization state can also be determined based, at least in part, on other input data such as positional data, user input, control signals, image data from an external imaging device, models of the instrument and/or patient motion, other sensor data, etc. The localization state can be dynamically updated (e.g., multiple times per second) as the operator drives the medical instrument within the anatomic region to provide real-time or near-real-time navigation guidance.

The image-based localization techniques disclosed herein may allow the medical instrument to be accurately tracked even without an initial registration, which is expected to simplify and shorten the overall procedure. Additionally, the techniques described herein are expected to provide numerous advantages compared to approaches that track the location of the medical instrument based on a single static registration and positional data for the instrument. In such conventional approaches, the tracked location may be inaccurate if the registration parameters do not correctly represent the mapping between the instrument position, the patient anatomy, and the 3D model, and/or if the 3D model does not accurately represent the actual anatomy. In contrast, the methods and systems described herein can use image data to continuously and accurately estimate the actual location of the medical instrument relative to the anatomy, and can dynamically update and display the estimated location and associated uncertainty to the operator. Moreover, if the operator drives the medical instrument to portions of the anatomy that are missing from or not accurately covered by the model, the methods and systems disclosed herein can use the image data to refine and/or extend the model, thus providing continued and accurate image-based guidance.

A. Embodiments of Processes for Dynamic Localization of a Medical Instrument

FIG. 1 is a flow diagram illustrating a method 100 for monitoring a localization state of medical instrument in accordance with various embodiments of the present technology. The method 100 is illustrated as a set of steps or processes 110-150. All or a subset of the steps of the method 100 can by implemented by any suitable computing system or device, such as a control system of a medical instrument system or device (e.g., including various components or devices of a robotic or teleoperated system), a workstation, a portable computing system (e.g., a laptop computer), and/or a combination thereof. In some embodiments, the computing system for implementing the method 100 includes one or more processors operably coupled to a memory storing instructions that, when executed, cause the computing system to perform operations in accordance with the steps 110-150. The method 100 is illustrated in the following description by cross-referencing various aspects of FIGS. 2-6.

The method 100 begins at step 110 with receiving a 3D model of an anatomic region of a patient. The model can represent an anatomic region in which a medical procedure is to be performed (e.g., the airways of the patient's lungs), and can represent the locations, shapes, and connectivity of the passageways and other structures within that region. In some embodiments, the model depicts one or more anatomic landmarks within the anatomic region. An anatomic landmark can be or include any portion of the anatomic region that may be readily identified and/or distinguished from other portions of the anatomic region, e.g., based on size, shape, color, and/or other suitable features. Examples of anatomic landmarks include, but are not limited to: branching points or regions (e.g., carinas), passageways (e.g., airways), blood vessels (e.g., near or adjacent to a tissue surface), protrusions (e.g., ridges), apertures (e.g., airway openings), or any other tissue structure with distinct features, or combinations thereof.

Figure 2:
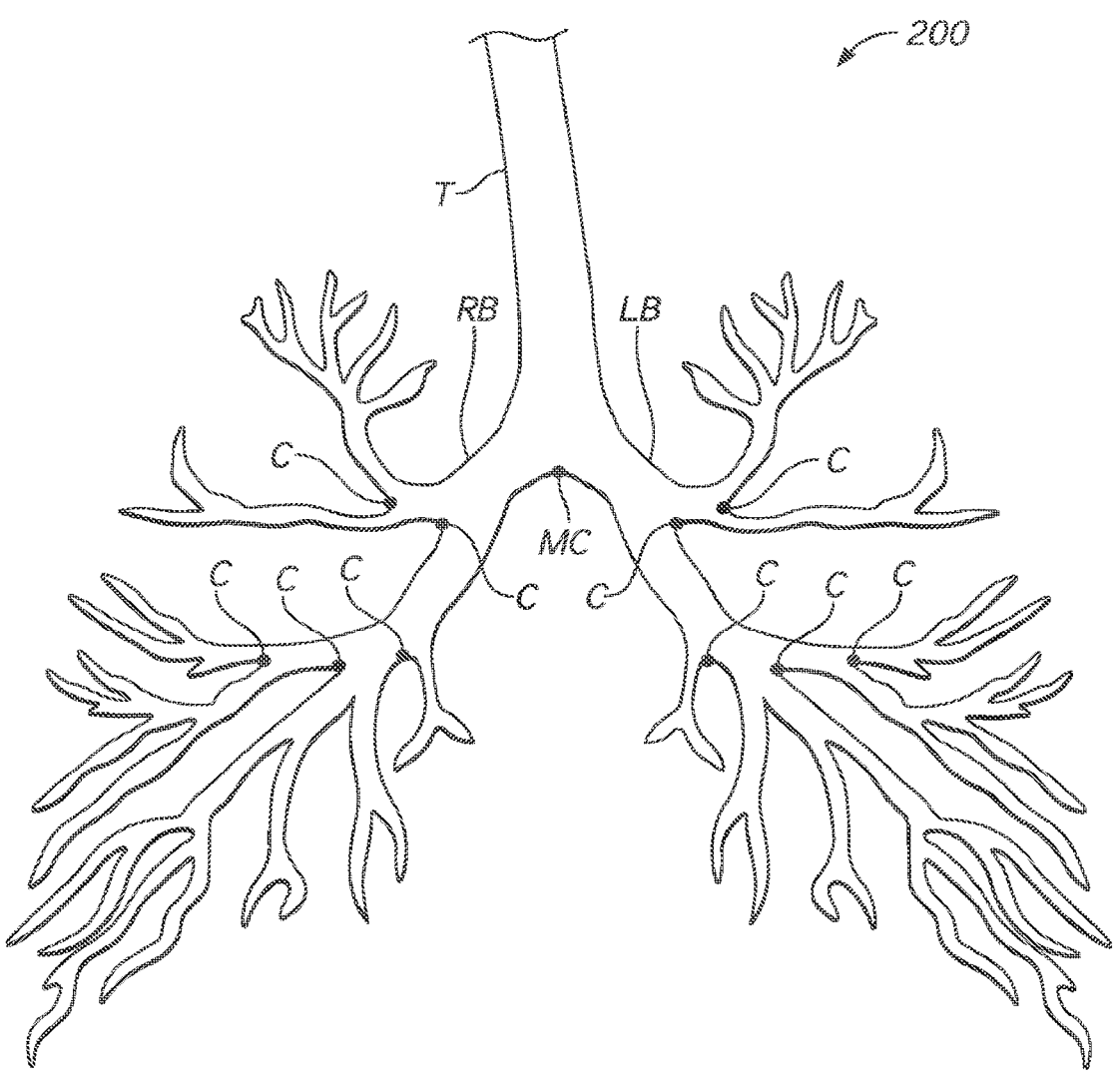
FIG. 2 illustrates examples of anatomic landmarks within the airways of a patient's lungs in accordance with various embodiments of the present technology.

FIG. 2 illustrates examples of anatomic landmarks within the airways 200 of a patient's lungs in accordance with various embodiments of the present technology. As can be seen in FIG. 2, the airways 200 include a main carina MC at the point or region where the trachea T branches into the left main bronchus LB and right main bronchus RB. The airways 200 also include a plurality of carinas C corresponding to the locations of branching points or regions in the airways C. As described in greater detail below, the localization techniques described herein can include imaging various portions of the airways 200, such as the main carina MC and/or one or more individual carinas C.

Referring again to FIG. 1, the 3D model of step 110 can be generated in a number of different ways. In some embodiments, for example, the 3D model is generated from preoperative and/or intraoperative image data of the anatomic region, such as computed tomography (CT) data, magnetic resonance imaging (MRI) data, fluoroscopy data, thermography data, ultrasound data, optical coherence tomography (OCT) data, thermal image data, impedance data, laser image data, nanotube X-ray image data, and/or other suitable data representing the patient anatomy. The image data can correspond to two-dimensional, 3D, or four-dimensional (e.g., time-based or velocity-based information) images. In some embodiments, for example, the image data includes two-dimensional images from multiple perspectives that can be combined into pseudo-3D images.

The 3D model can be generated by segmenting graphical elements in the image data that represent anatomic features. During the segmentation process, pixels or voxels generated from the image data may be partitioned into segments or elements and/or be tagged to indicate that they share certain characteristics or computed properties such as color, density, intensity, and texture. The segments or elements associated with anatomical features of the patient are then converted into a segmented anatomic model, which is generated in a model or image reference frame. To represent the model, the segmentation process may delineate sets of voxels representing the anatomic region and then apply a function, such as a marching cube function, to generate a 3D surface that encloses the voxels. The model may be made by generating a mesh, volume, or voxel map. Additionally or alternatively, the model may include a centerline model that includes a set of interconnected line segments or points extending through the centers of the modeled passageways. Where the model includes a centerline model including a set of interconnected line segments, those line segments may be converted to a cloud or set of points. By converting the line segments, a desired quantity of points corresponding to the interconnected line segments can be selected manually or automatically.

In some embodiments, the 3D model is registered to the anatomic region. The registration can provide a correspondence between the patient anatomy and the model that may be used to estimate the location of a medical instrument within the anatomic region, as described in greater detail below. The registration can be performed using any suitable technique, such as a point-based iterative closest point (ICP) technique, as described in U.S. Provisional Pat. App. Nos. 62/205,440 and No. 62/205,433, which are both incorporated by reference herein in their entireties. For example, the operator can survey the anatomic region with a medical instrument to generate a set of coordinate points (e.g., a point cloud), and the registration algorithm can rotate, translate, or otherwise manipulate the coordinate points by rigid and/or non-rigid transforms to align them with the data points of the model. In other embodiments, however, the subsequent steps of the method 100 can be performed without determining a registration between the 3D model and the anatomic region. In such embodiments, the operator may not need to conduct an initial survey of the anatomic region to collect data points for registration, and can begin performing the medical procedure immediately.

At step 120, the method 100 continues with obtaining image data of a portion of the anatomic region. The image data can be obtained by an image capture device (e.g., an endoscopic camera) configured to obtain images (e.g., still images, video image frames) from within the patient. In some embodiments, for example, the image capture device is carried by a medical instrument inserted within the anatomic region. For example, as discussed in greater detail below with reference to FIGS. 7-13, the image capture device can be included in and/or mounted on a portion of the medical instrument, e.g., at or near the distal end portion of the medical instrument. As such, the pose of the image capture device can be identical or generally similar to the pose of the corresponding portion of the medical instrument. Additionally, as described further below with respect to FIGS. 7-13, the medical instrument can be deployed into the anatomic region via an elongate device (e.g., a steerable catheter), such that the pose of at least a portion of the medical instrument is identical or generally similar to a pose of the corresponding portion of the elongate device. Accordingly, any description herein regarding a position, orientation, pose, location, insertion depth, etc. of the image capture device can also refer to a position, orientation, pose, location, insertion depth, etc. of a corresponding portion of the medical instrument and/or elongate device, and vice-versa. Similarly, any description herein regarding movement of the image capture device (e.g., translating, rotating) can also refer to movement of a corresponding portion of the medical instrument and/or elongate device, and vice-versa.

In some embodiments, step 120 includes capturing images once the image capture device has been introduced into the anatomic region and moved sufficiently close to a target anatomic structure, such as an anatomic landmark (e.g., a carina). The process of determining whether the image capture device is sufficiently close to the target can be performed manually, automatically, or semi-automatically. For example, the operator can manually initiate image capture when it is determined that the image capture device is sufficiently close to the target anatomic structure, e.g., based on image data from the image capture device, insertion depth data, positional data, image data of the image capture device and/or the medical instrument from an external imaging device, etc. In some embodiments, the operator views images generated by the image capture device to determine whether the image capture device is at or near the target anatomic structure (e.g., within the lungs or trachea) and/or whether the target anatomic structure is within the field of view of the image capture device. Once the image capture device is positioned appropriately, the operator can initiate imaging by providing a user input, such as pushing a button, typing or speaking a command, etc.

As another example, step 120 of the method 100 can include automatically detecting whether the image capture device is sufficiently close to the target anatomic structure for imaging (e.g., within 10 cm, 5 cm, 4 cm, 3 cm, 2 cm, 1.5 cm, 1 cm, or 0.5 cm of the target anatomic structure). In such embodiments, a computing system (or any other suitable system or device) can receive and analyze images generated by the image capture device to detect whether the image capture device is at a desired location and/or whether the target anatomic structure is within the field of view. The image analysis can be performed using any suitable technique, including machine learning algorithms (e.g., convolutional neural networks (CNNs)), circle detectors (e.g., the Hough transform), and/or other computer vision techniques. For instance, the analysis can include detecting anatomic landmarks and/or other structures in the image data (e.g., trachea, main carina, other carinas) based on features such as size, shape, number of visible openings (e.g., one visible opening when in the trachea versus two visible openings when near the main carina), changes in color, changes in texture, and so on. Proximity can additionally or alternatively be determined based on other types of data, such as insertion depth data, positional data, image data from an external imaging device, etc. For example, the image capture device can be considered to be sufficiently close to the target anatomic structure once the insertion depth of the image capture device and/or the medical instrument carrying the image capture device exceeds a predetermined threshold value. Once the image capture device is in proximity to the target anatomic structure, the system can automatically initiate imaging. Alternatively, the system can prompt the operator to initiate imaging, e.g., via textual, graphical, audio, and/or other types of output.

Optionally, in embodiments where the image capture device and medical instrument are introduced into the anatomic region via a separate introducer component (e.g., an elongate tube such as an endotracheal (ET) tube, etc.), step 120 can include automatically detecting whether the image capture device has been advanced past the distal end portion of the introducer component. For example, the detection process can use computer vision techniques (e.g., machine learning algorithms, circle detectors) to identify when the image capture device has exited the distal end of an ET tube, e.g., based on shape, changes in the size of visible openings (e.g., smaller when in the ET tube, larger when in the trachea), changes in color, changes in texture, etc. Optionally, the ET tube can include visual indicators, such as markings, patterning, color, etc. at or near its distal end, and the visual indicators can be used to determine the location of the image capture device relative to the end of the ET tube. Additional examples of visual indicators for an ET tube are described in further detail in U.S. Patent Application Publication No. 2018/0235709 (filed on Aug. 11, 2016) (disclosing systems and methods of registration for image-guided surgery), which is incorporated by reference herein in its entirety. Once the image capture device is deployed sufficiently far out of the introducer component, the system can automatically initiate imaging, or prompt the operator to do so.

In other embodiments, step 120 can involve initiating imaging at the start of the medical procedure (e.g., once the image capture device is powered on, once the operator begins driving the medical instrument, etc.), rather than waiting until the image capture device is close to the target anatomic structure. In such embodiments, the method 100 can include discarding image data that is irrelevant, erroneous, or otherwise not suitable for localization (e.g., images taken before the image capture device enters the anatomic region and/or while the image capture device is still in the ET tube) in subsequent process steps. For example, images that cannot be matched to any portion of the 3D model can be discarded, since such images are likely to have been taken while the image capture device was outside of the anatomic region. As another example, the discarded images can include images that produce 3D data that is clearly inconsistent with the 3D model (e.g., the centerline of the 3D data differs significantly from the centerline of the 3D model). In yet another example, step 120 can include tracking the location of the image capture device during imaging, and using the location data to discard images that were likely taken outside the anatomic region.

During the imaging process, the image capture device can obtain a plurality of images of the target anatomic structure (e.g., a carina or other anatomic landmark), such as at least two, three, four, five, or more images. In some embodiments, some or all of the images are taken with the image capture device in different poses (e.g., different positions and/or orientations) relative to the target, such that the resulting images represent different views of the target. For example, images can be taken from at least two, three, four, five, or more different poses relative to the target. In other embodiments, however, the image capture device may take only a single image of the target from a single pose.

The number of images, as well as the amount of spatial offset and/or motion between the images, can be configured to allow the structure of the target anatomic structure to be reconstructed from the images, e.g., using computer vision and/or machine-learning based techniques as discussed in greater detail below. For example, the translational offset between images can be greater than or equal to, for example, 1 mm, 2 mm, 3 mm, 4 mm, 5 mm, 6 mm, 7 mm, 8 mm, 9 mm, 10 mm, 15 mm, 20 mm, 25 mm, 30 mm, 35 mm, 40 mm, 45 mm, or 50 mm. As another example, the rotational offset between images can be greater than or equal to, for example, 1 degree, 5 degrees, 10 degrees, 15 degrees, 20 degrees, 30 degrees, 40 degrees, 45 degrees, 50 degrees, or 60 degrees. The number of images and/or amount of offset between images may also vary based on the size of the local anatomy. For example, the image capture device can take more images with more spatial offset if the target anatomic structure is located within a relatively large anatomic passageway. Conversely, the image capture device can take fewer images with less spatial offset if the target anatomic structure is located within a smaller passageway. In some embodiments, when imaging an anatomic structure in a narrow passageway with limited room for maneuvering, the image capture device may simply be moved in and out of the passageway during imaging. Conversely, when imaging an anatomic structure in a wider passageway, the image capture device can also be turned in different directions relative to the structure.

Figure 3:
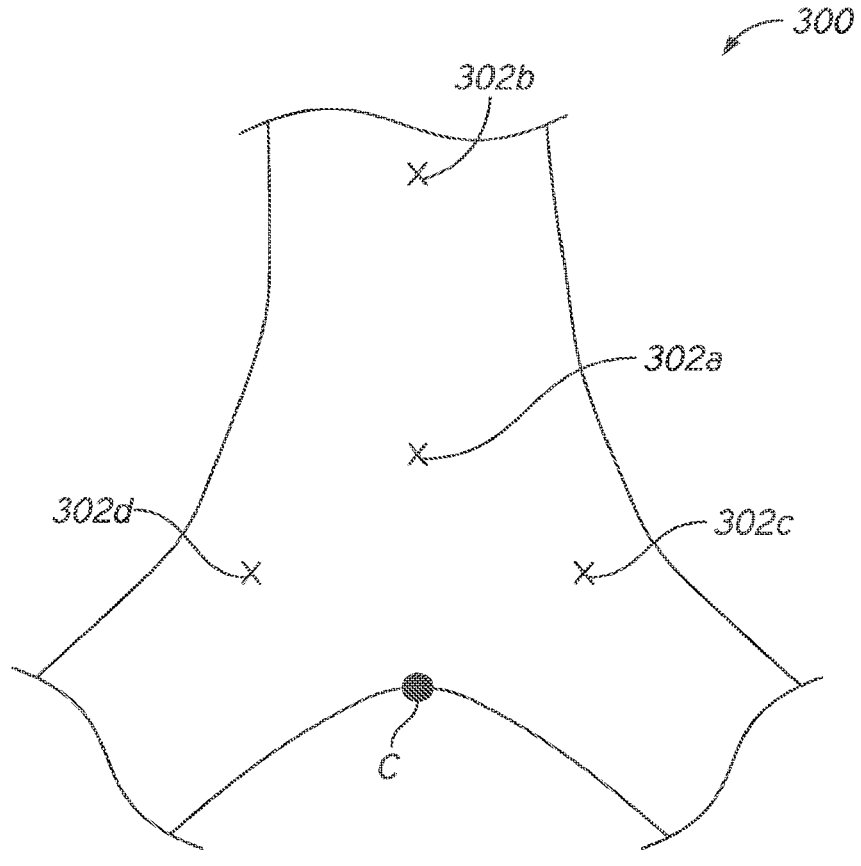
FIG. 3 illustrates a portion of a patient's airways including a plurality of imaging locations in accordance with various embodiments of the present technology.

FIG. 3 illustrates a portion 300 of a patient's airways and FIGS. 4A-4D illustrate a plurality of images 400a-400d of the portion 300, in accordance with various embodiments of the present technology. Referring first to FIG. 3, the airways include an anatomic landmark (e.g., a carina C). An image capture device (not shown) can obtain a plurality of images of the carina C from a corresponding plurality of locations 302 (four are identified in FIG. 3 as 302a-d) relative to the carina C. For example, the image capture device can obtain image 400a (FIG. 4A) from location 302a at a first distance from the carina C, and image 400b (FIG. 4B) from location 302b at a second, greater distance from the carina C. As another example, the image capture device can obtain image 400c (FIG. 4C) from location 302c near a first (e.g., left) side of the carina C, and image 400d (FIG. 4D) from location 302d near a second (e.g., right) side of the carina C. In additional embodiments, the number, position, and/or orientation of the locations 302 may vary. Although FIGS. 3-4D illustrate imaging of a carina C, in other embodiments, the techniques described herein can alternatively or additional include obtaining image data of a different anatomic structure, such as a section of an airway or other anatomic passageway that is spaced apart from any carinas.

Referring again to FIG. 1, the image data of step 120 can be obtained in various ways, such as manually by the operator, automatically by a computing system (or other suitable system or device), or a combination thereof. In some embodiments, for example, the operator manually navigates the image capture device to different locations and obtains one or more images at each location. The system can provide instructions to guide the operator in navigating and obtaining suitable images. For example, the system can instruct the operator to move the image capture device to different positions and/or orientations relative to the target anatomic structure (e.g., "drive X distance forward," "drive in Y direction," "rotate Z degrees," etc.). As another example, the system can simply instruct the operator to collect a certain number of images of the target anatomic structure, without specifying specific positions and/or orientations of the image capture device. The instructions may be output as text, graphics (e.g., arrows or other visual indicators), audio, or any other suitable format.

Optionally, the system can track the location of the image capture device and update the instructions based on how the operator moves the image capture device. In some embodiments, the system detects whether the operator has obtained sufficient images at a specified location, and, if so, instructs the operator to drive the image capture device to the next location. If the system detects that there are gaps in the image data, the system can instruct the operator to obtain additional images, and, optionally, direct to the operator to specific locations where the additional images should be taken.

In some embodiments, the system automatically moves the image capture device to different locations relative to the target anatomic structure. For example, the system can determine a sequence of imaging locations (e.g., based on the size and/or shape of the local anatomy) or can use a predefined sequence (e.g., a predefined sequence of translations and/or rotation). Once the image capture device is at a specified location, the system can either automatically take one or more images from that location, or can prompt the operator to do so. Subsequently, the system can automatically move the image capture device to the next location. This process can be repeated until images have been taken from each location in the sequence.

In addition to obtaining image data, step 120 can also include recording the pose (i.e., position and orientation) of the image capture device when each image was taken. The pose data can be generated by one or more sensors associated with the image capture device, such as shape sensors, pose sensors, positional sensors, location sensors (e.g., electromagnetic (EM) sensors), etc. In such embodiments, the sensors can be coupled to the image capture device, or can be carried by a medical instrument or elongate device associated with the image capture device. The pose data can also be determined based on other information, such as insertion depth data, images from an external imaging device, control inputs from the operator, etc. The pose data can be used in combination with the image data in the subsequent process steps discussed below.

Additionally, step 120 can include using the pose data to monitor the imaging process and, optionally, outputting appropriate instructions to the operator based on the pose data. For example, the system can determine whether sufficient images have been obtained for a particular pose and, if so, prompt the operator move the image capture device to a different pose. As another example, the system can detect whether images have not been taken from certain poses and instruct the operator to capture images from those poses. The system can also use the pose data as feedback when automatically moving the image capture device to different poses, as discussed above.

Optionally, step 120 can involve implementing imaging techniques configured to ensure that the images contain sufficient features for the image analysis processes described in detail below. In some embodiments, for example, the target anatomic structure can be illuminated with different wavelengths of light (e.g., infrared, near-infrared, visible, etc.) to add and/or enhance features in the resulting images. For example, certain tissue structures such as blood vessels may be more apparent under certain wavelengths of light. Alternatively or in combination, structured light techniques can be used to add and/or enhance features of the anatomy by projecting a known geometric pattern onto the imaging target (e.g., grid, stripes, bars, etc.).

Step 120 can also include providing feedback to assist the operator in collecting higher quality images by providing feedback (e.g., via a graphical user interface and/or other output). For example, the feedback can alert the operator of issues that may compromise image quality such as blurring, fogging, and/or obstruction of the image capture device (e.g., by blood and/or other bodily fluids). The feedback can also instruct the operator to perform one or more recommended actions to resolve the issue, such as defogging the image capture device, clearing obstructions from the image capture device, moving the image capture device to a different location, etc. Optionally, the system can also perform corrective actions automatically, e.g., activating defogging and/or cleaning mechanisms to clear the image capture device. As another example, in embodiments where the imaging is performed within narrow and/or tortuous passageways (e.g., airways), the feedback can periodically remind the operator to keep the image capture device away from the walls of the passageways to avoid obstructing the field of view. In some embodiments, the system is configured to detect whether the image capture device is too close to the walls of the passageways (e.g., using image analysis, sensors to detect friction and/or resistance to movement, etc.) and prompt the operator to take corrective action, if appropriate. Additionally, the system can automatically detect and tag poor quality images (e.g., blurry images, images with obstructions) so they can be excluded in subsequent process steps.

At step 130, the method 100 continues with determining a localization state of a medical instrument in the anatomic region, based on the image data. As discussed above, the medical instrument can include or otherwise be associated with the image capture device that obtained the image data. The localization state can include an estimated location of a portion of the medical instrument, such as the distal end portion of the medical instrument and/or the portion carrying the image capture device. The estimated location can be expressed as a set of coordinates (e.g., a 3D coordinate vector), a location in the 3D model or other representation of the anatomic region (e.g., an airway tree), or a combination thereof. The estimated location can include an estimated position (e.g., x, y, and/or z coordinates), an estimated orientation (e.g., roll, pitch, and/or yaw), or a combination thereof.

The localization state can also include at least one uncertainty parameter for the estimated location. The uncertainty parameter can be a specific value, range of values (e.g., upper and/or lower bounds), or any other representation of the degree of uncertainty associated for the estimated location. For example, the uncertainty parameter can be or include a range of values corresponding to a particular confidence level, such as a 75%, 80%, 85%, 95%, or 99% confidence level. In some embodiments, step 130 further includes calculating a probability distribution for the instrument location (e.g., a Gaussian distribution), with the estimated location corresponding to the mean value or vector of the probability distribution, and the uncertainty parameter corresponding to a confidence interval, covariance matrix, or similar value or data structure.

The localization state of the medical instrument can be determined from the image data in a number of different ways. For example, at optional step 135 (which can be a sub-process of step 130), the method 100 includes using the image data to estimate the location of the medical instrument relative to one or more anatomic landmarks (e.g., carinas, passageways, etc.), also referred to herein as anatomic localization. An anatomic localization process can involve obtaining one or more images of an anatomic landmark, analyzing the image(s) to associate (e.g., match) the anatomic landmark to a corresponding model landmark in the 3D model, and mapping the location of the medical instrument to the location of the model landmark within the model. Thus, as the medical instrument navigates past various anatomic landmarks in the patient, the location of the medical instrument can be tracked with respect to the corresponding model landmarks in the 3D model.

Figure 5A:
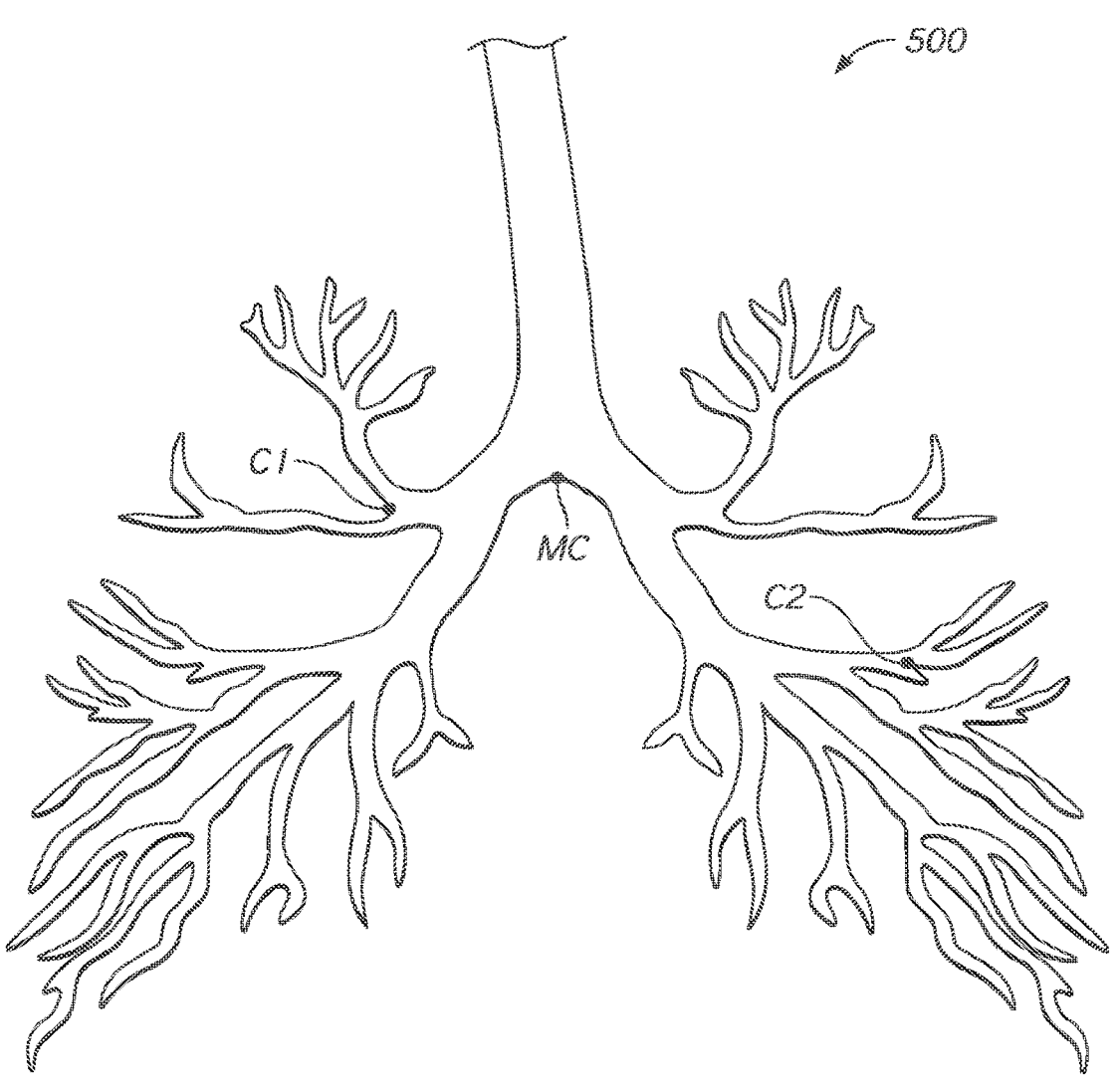
FIG. 5A illustrates a model of a patient's airways including a plurality of model landmarks in accordance with various embodiments of the present technology.
Figure 5B:
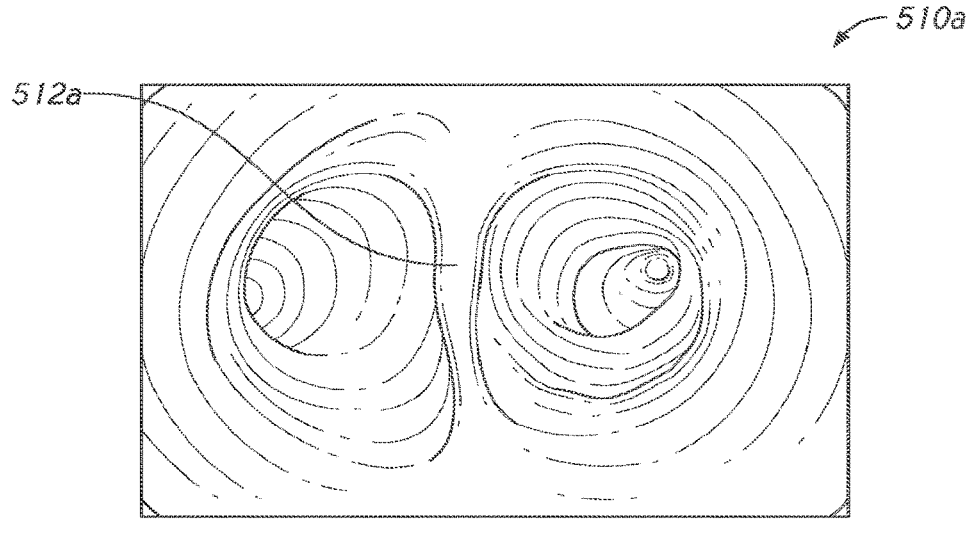
FIGS. 5B-5D illustrate a plurality of images that may be associated with the model landmarks of FIG. 5A in accordance with various embodiments of the present technology.
Figures 5C, 5D:
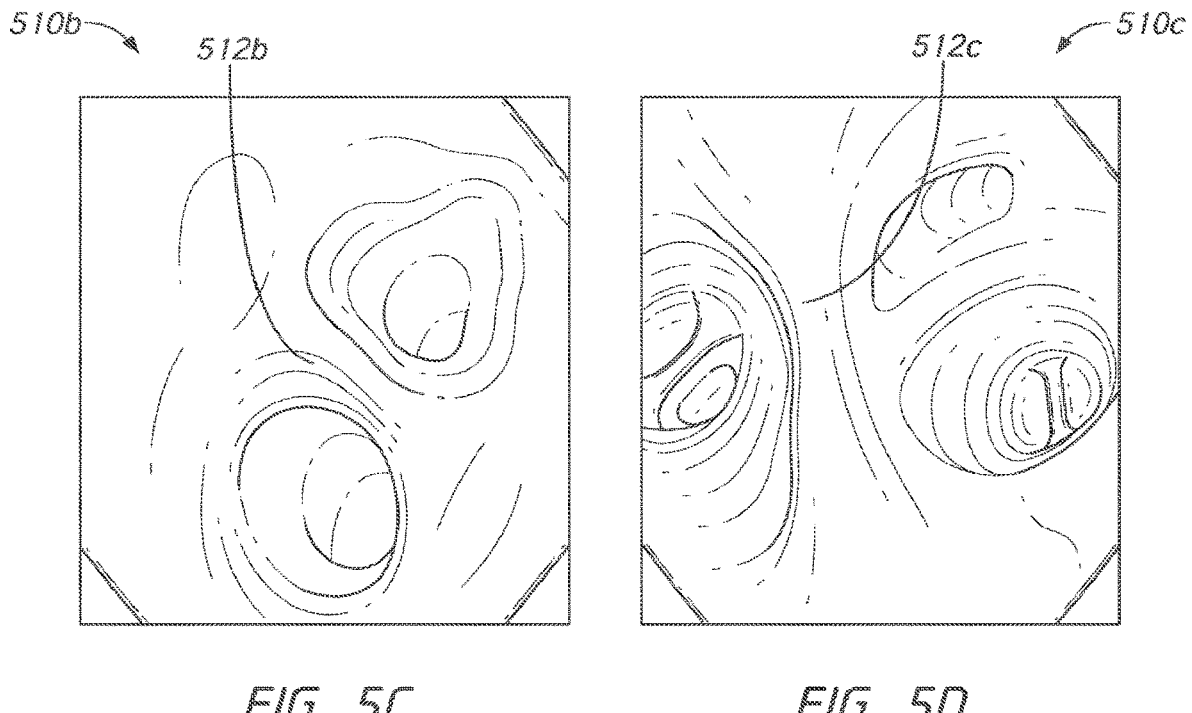

FIG. 5A, for example, illustrates a model 500 of a patient's airways and FIGS. 5B-5D illustrate a plurality of images 510a-c of the airways, in accordance with various embodiments of the present technology. Referring first to FIG. 5A, the model 500 includes a plurality of carinas or branching points, such as a main carina MC, a first carina C1, and a second carina C2. Referring next to FIGS. 5B-5D together, the images 510a-c can be obtained by an image capture device carried by a medical instrument within the patient's airways. In some embodiments, the images 510a-c are analyzed to identify features of the carinas 512a-c, such as the carina ridge, openings (e.g., bifurcations, trifurcations), branching angles, surrounding airways, and/or other local tissue structures or features. Based on the identified features, the carinas 512a-c shown in the images 510a-c of FIGS. 5B-5D can each be associated with a corresponding carina in the model 500. For example, carina 512a of image 510a (FIG. 5B) can be matched to the main carina MC (FIG. 5A), carina 512b of image 510b (FIG. 5C) can be matched to the first carina C1 (FIG. 5A), and carina 512c of image 510c (FIG. 5D) can be matched to the second carina C2

(FIG. 5A). Although FIGS. 5B-5D show a single image for each carina, this is merely for illustrative purposes, and carina matching can be performed using multiple images of each carina as discussed in detail below.

The associations between the carinas 512a-c and the carinas in the model 500 can be used to estimate the location of the medical instrument. For example, based on the matching results described above, the medical instrument was at or near the main carina MC when image 510a (FIG. 5B) was obtained; the medical instrument was at or near the first carina C1 when image 510b (FIG. 5C) was obtained; and the medical instrument was at or near the second carina C2 when image 510c (FIG. 5D) was obtained. Thus, as the medical instrument is driven through the patient's airways, the location of the medical instrument can be estimated and tracked with respect to the carinas in the model 500.

Referring again to FIG. 1, the image analysis for the anatomic localization process of step 135 can be performed in various ways. For example, step 135 can involve analyzing images of an anatomic landmark using computer vision techniques and/or machine learning techniques to identify distinguishing features. In some embodiments, for example, the image analysis includes detecting one or more features of the anatomic landmark from the image data, such as the shape, size, color, texture, etc. of tissue structures such as ridges, openings, passageways, etc. The detected features can then be compared to features of one or more model landmarks to identify the corresponding model landmark (if any). Alternatively or in combination, the image analysis can use a machine learning algorithm that has been trained to identify and/or categorize particular anatomic landmarks based on image data. Subsequently, the image analysis results can be used to match the anatomic landmark to a corresponding model landmark.

In some embodiments, step 135 includes using 2D- and/or 3D-based approaches to identify an association between the anatomic landmark and the matching model landmark. For example, a 2D-based approach can include determining a correspondence between one or more images of the anatomic landmark obtained in step 120 (also referred to herein as "real images") and one or more images of model landmarks generated from the 3D model (also referred to herein as "virtual views" or "virtual images"). Each virtual view can be a 2D image of a model landmark from a simulated viewpoint in the model. The real images and virtual views can be analyzed to detect and extract 2D image features, such as points, edges, corners, blobs, ridges, changes in intensity, changes in color, etc. The features can include sparse features, dense features, or a combination thereof. The features from the real images and virtual views can then be compared to identify similar and/or matching features (e.g., features that are present in both the real images and the virtual views). If the real images of the anatomic landmark are highly similar to the virtual views of the model landmark (e.g., share a large number of similar and/or matching features), the anatomic landmark can be associated with (e.g., matched to) the model landmark. Optionally, the matching process can use a 2D image alignment algorithm (e.g., an inverse-compositional Lucas-Kanade algorithm), such that the anatomic landmark is associated with a model landmark if the virtual views of the model landmark can be successfully aligned to the real images of the anatomic landmark.

As another example, a 3D-based approach can include generating a 3D representation of an anatomic landmark from the image data of step 120, then using the 3D representation to identify the corresponding model landmark. The 3D representation can be a reconstruction of the 3D shape of the anatomic landmark and surrounding tissue structures. The 3D representation can be or include a surface or mesh model, a 3D point cloud, or any other format for conveying 3D shape data. The 3D representation can be generated using any suitable technique for determining 3D depth information from one or more 2D images, such as structure from motion, shape from shading, and/or machine learning-based techniques (e.g. single shot depth estimation, end-to-end depth reconstruction, etc.). For example, a machine learning model (e.g., a CNN) can be trained to generate a 3D depth map of the anatomy from one or more 2D images. As another example, 3D depth data can be estimated from 2D images using sparse or dense depth reconstruction techniques. Additionally, the pose data of the image capture device can be used to determine scale information for the 3D representation.

Once the 3D representation has been generated, the 3D representation can be compared to the 3D model of the anatomy to identify a matching model landmark. In some embodiments, the 3D representation of the anatomic landmark is aligned to the model using a 3D alignment or registration algorithm (e.g., ICP algorithm, an ICP with scaling algorithm, a surface- or mesh-based ICP algorithm, a coherent point drift algorithm, or a machine learning-based algorithm such as PointNetLK). If the 3D representation can be successfully aligned to a model landmark, the anatomic landmark depicted in the 3D representation can be associated with (e.g., matched to) the model landmark. Alternatively or in combination, the anatomic landmark can be matched to a model landmark based on similar surface features. In such embodiments, the matching process can include identifying and extracting surface features in the 3D representation, then comparing the identified features to surface features of one or more model landmarks to assess the degree of similarity. If the anatomic landmark is highly similar to the model landmark (e.g., share a large number of similar and/or matching surface features), the anatomic landmark can be matched to the model landmark.

Optionally, if the 3D representation cannot be successfully registered to any model landmarks, this may indicate that the imaged anatomy is outside of the bounds of the model and/or inaccurately represented in the model. In such embodiments, the 3D representation can be used to extend and/or modify the model. For example, if the system and/or operator detects that the portion of the anatomic region depicted in the 3D representation is outside of or otherwise different from the portion of the anatomic region represented in the model, the 3D representation can be added to the model in order to extend the model to include the new portion. As another example, if the system and/or operator determines that the structure of the anatomy in the 3D representation is inconsistent with the structure represented in the model, the model can be updated by replacing the appropriate portion of the model with the 3D representation. As such, the techniques described herein may provide more accurate and flexible navigation guidance for the operator, compared to approaches using a static model that cannot be updated during the procedure.

In some embodiments, step 135 further includes using location-based filtering to select a subset of model landmarks for comparison to the anatomic landmark (e.g., in either the 2D—based or 3D-based approaches discussed above). As discussed above, the images of the anatomic landmark can be associated with pose data generated by one or more sensors (e.g., shape sensors, pose sensors, positional sensors, location sensors). For example, the pose data can represent a position and/or orientation of the image capture device when taking the images of the anatomic landmark. The pose data can be analyzed to estimate a location of the anatomic landmark (e.g., a particular side, quadrant, airway generation, and/or lobe of the lungs; a set of three-dimensional coordinates; etc.). The matching process can include selecting model landmarks that are located at or near the estimated location, since those landmarks are more likely to match the anatomic landmark. Conversely, the matching process can exclude model landmarks that are located away from the estimated location, since those are less likely to match the anatomic landmark. This approach can improve the efficiency and speed of the matching process by limiting the analysis to model landmarks that are sufficiently close to the estimated location of the anatomic landmark.

Optionally, step 135 can include outputting feedback to the operator if the image data is insufficient for the matching process. For example, if the anatomic landmark cannot be successfully matched to any model landmarks due to inadequate and/or incomplete image data, the feedback can instruct the operator to obtain additional images of the anatomic landmark. The additional image data can be used in combination with or as an alternative to the previous image data to re-run the matching process.

Referring again to step 130 of FIG. 1, the localization state can also be determined using other types of input data besides image data. For example, step 130 can include receiving positional data of the medical instrument from one or more sensors (e.g., positional sensors, shape sensors, pose sensors, location sensors, EM sensors, etc.), and using the positional data on its own or in combination with other data (e.g., a registration) to generate an estimated location for the instrument. As another example, step 130 can include using control signals for the medical instrument to determine the localization state, e.g., if the instrument is commanded to move in a particular direction, the instrument's position and/or orientation can be assumed to change accordingly when calculating the estimated location. In yet another example, the operator can provide input that identifies the location of the instrument (e.g., confirming that the instrument is near a particular anatomic landmark) and/or indicates whether the estimated location determined is likely to be correct or incorrect. The estimated location and/or uncertainty parameter can be modified based on the operator input, such as by increasing the amount of uncertainty if the operator disagrees with the estimated location, and decreasing the amount of uncertainty if the operator confirms the estimated location. In a further example, the localization state can be estimated using image data from an external imaging device (e.g., an intraoperative C-arm cone-beam CT, fluoroscopy, positron emission tomography (PET), etc.) and/or another internal imaging device (e.g., endobronchial ultrasound (EBUS). Other types of input data suitable for use in determining localization state include, but are not limited to: other types of sensor (e.g., data from a reference sensor at a known external or internal location, such as an optical sensor), models of the medical instrument (e.g., a model of the instrument's response to control inputs), and/or models of patient motion (e.g., respiratory phase models). In some embodiments, the localization state is determined using multiple different types of input data (e.g., at least two, three, four, five, or more data types).

Step 130 can also include using previous localization states as inputs when determining the current localization state of the medical instrument. In some embodiments, localization states generated in previous timesteps (e.g., the most recent timestep; or the past 2, 5, 10, 20 or more timesteps) are recorded and used the to inform the current state estimate. For example, the current location of the instrument can be assumed to be within a particular range of the previous location (e.g., based on the maximum movement speed of the instrument). As another example, the uncertainty level for the current estimate may increase if the previous estimates were highly uncertain; conversely, the uncertainty level for the current estimate may decrease if the previous estimates were highly certain.

In some embodiments, step 130 includes generating multiple localization state estimates from the multiple input data types. For example, a first state estimate can be generated from the image data (e.g., using the anatomical matching process described above), a second state estimate can be generated from the positional data, a third state estimate can be generated from the control signals, and so on. Each state estimate can be generated from a single type of input data. Alternatively, some or all of the state estimates can be generated from a plurality of different input data types (e.g., two, three, four, or more different types). Each individual state estimate can include a respective estimated location and respective uncertainty parameter. Subsequently, the individual state estimates can be combined to determine the overall or final localization state. The state estimates can be combined in various ways, such as using a Kalman filter, a factor graph, a particle filter, or any other suitable sensor fusion or data fusion algorithm.

Optionally, the operator can be prompted to obtain additional data if the calculated uncertainty parameter is too high (e.g., greater than a predetermined threshold). For example, the operator can be instructed to obtain additional images of the local anatomy (e.g., one or more nearby anatomic landmarks), and can recalculate or update the localization state based on the new image data. If the anatomy at the current location is not sufficiently distinctive for localization purposes, the operator can be instructed to navigate to a different location to capture image data. Additionally, if certain data sources produced highly uncertain state estimates, the localization state can be recalculated without the input data from those data sources and/or using input data from other data sources that may be more reliable.

At step 140, the method 100 includes dynamically updating the localization state as the operator navigates the medical instrument within the anatomic region, e.g., by repeating the processes of steps 120 and/or 130. For example, when the medical instrument is driven to a new portion of the anatomy, the image capture device can obtain images of the new portion (e.g., anatomic landmark), and the new images can be used to determine the new localization state of the instrument (along with other input data, if desired). As another example, if new input data is received during the procedure (e.g., new positional data, user inputs, external images, etc.), the localization state of the medical instrument can be recalculated based on the new input data. The localization state can be continuously updated at a sufficiently high rate to provide real-time or near-real-time tracking of the medical instrument. For example, the update rate can be at least 15 times per second, 30 times per second, or 60 times per second. In some embodiments, updates are performed at predetermined time intervals. In other embodiments, the update rate may vary. For instance, the update rate can depend on the data rates of the image capture device and/or other sources of input data for the localization state estimate. In such embodiments, the localization state may be updated whenever new image data and/or other input data is available. Optionally, the update rate can vary based on the motion of the medical instrument, e.g., the localization state is updated more frequently when the medical instrument is moving, and less frequently when the medical instrument is stationary.

At step 150, the method 100 optionally includes displaying a graphical representation of the localization state. The graphical representation can include at least one visual indicator showing the estimated location and, optionally, at least one visual indicator representing the uncertainty parameter. The operator can refer to the graphical representation during the procedure when performing an image-guided medical procedure in the anatomic region. For example, the graphical representation can help the operator navigate the medical instrument to a target location in the anatomic region (e.g., a target lesion or other biopsy site).

Figure 6:
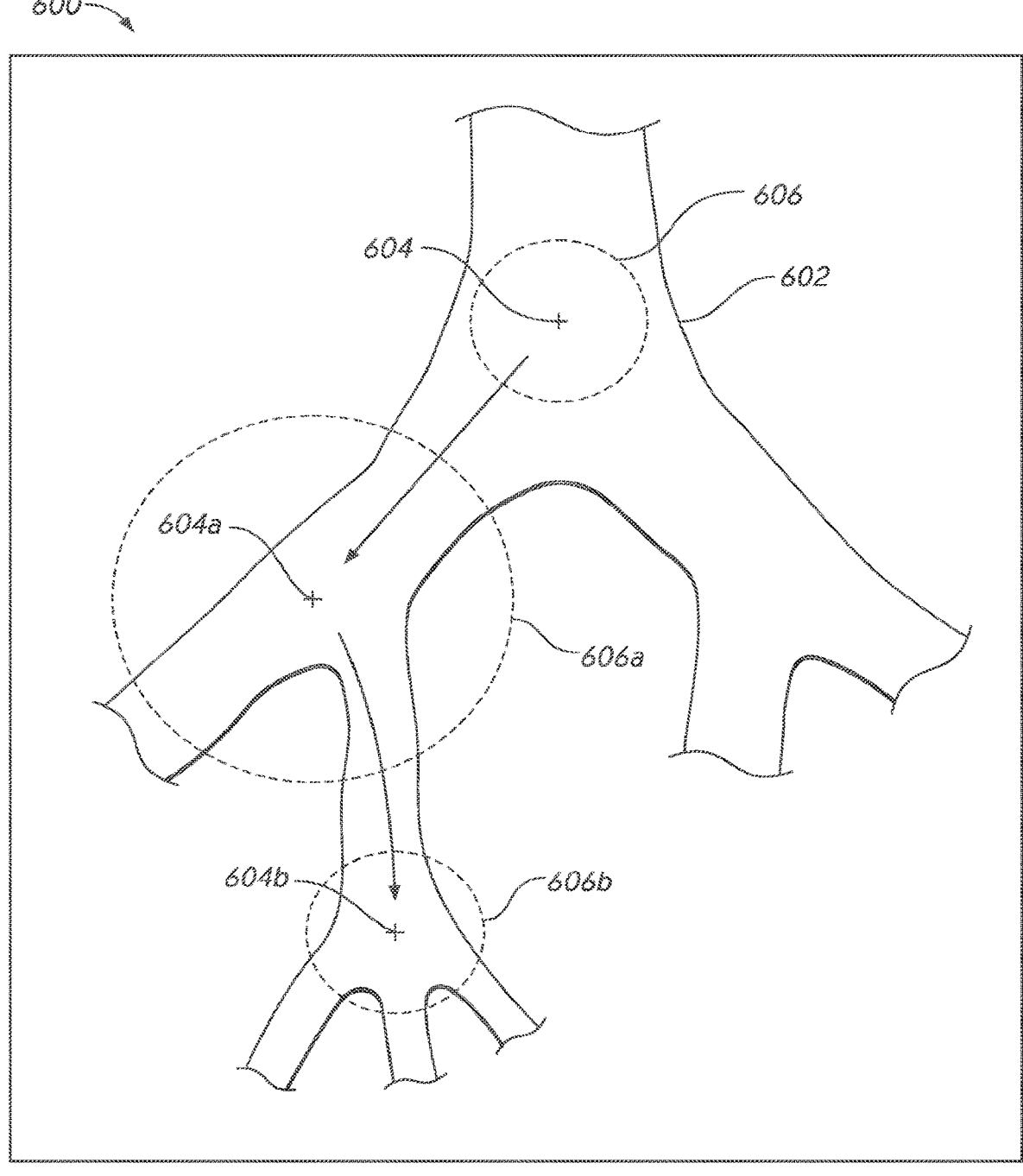
FIG. 6 is a schematic illustration of graphical user interface for displaying a localization state of a medical instrument in accordance with various embodiments of the present technology.

FIG. 6 illustrates a graphical user interface 600 ("interface 600") for displaying the localization state of a medical instrument in accordance with various embodiments of the present technology. The interface 600 includes a graphical representation of the anatomic region ("anatomical representation 602"), such as an airway map or tree, a 2D model, a 3D model, etc. The interface 600 also includes a first visual indicator 604 overlaid onto the anatomical representation 602 to show the estimated location of the medical instrument (e.g., the estimated location of a distal end portion or other portion of the instrument). The first visual indicator 604 can simply be a marker at the estimated location, or can be a graphical representation of a portion of the medical instrument (e.g., the distal end of the instrument). The interface 600 can also include a second visual indicator 606 representing the uncertainty parameter associated with the estimated location. In the illustrated embodiment, the second visual indicator 606 is a region (e.g., a bubble) surrounding the first visual indicator 604 to indicate a range of probable locations for the medical instrument. The size of the region can change based on the amount of uncertainty, e.g., the size increases with greater uncertainty and decreases with lower uncertainty. Although FIG. 6 illustrates the second visual indicator 606 as having a circular shape, in other embodiments the second visual indicator 606 can have a different shape (e.g., elliptical, square, rectangular, polygonal, etc.).

The first and second visual indicators 604, 606 can be updated to reflect changes in the estimated localization state as the operator drives the medical instrument in the anatomy. In the illustrated embodiment, for example, when the medical instrument moves to a first location 604a, the level of uncertainty increases and is conveyed to the operator by an increase in the size of the second visual indicator 606a; when the medical instrument moves to a second location 604b, the level of uncertainty decreases and is conveyed to the operator by a decrease in the size of the second visual indicator 606b; and so on. The interface 600 can be continuously updated at a sufficiently high rate to provide a real-time or near-real-time graphical representation of the localization state (e.g., at least 15 times per second, 30 times per second, 60 times per second, etc.).

Although in FIG. 6 the uncertainty parameter is displayed as uncertainty in the location of the medical instrument via the second visual indicator 606, the interface 600 can also use other techniques to visually represent the degree of uncertainty. For example, the uncertainty parameter can alternatively or additionally be depicted as uncertainty in the locations of anatomic structures relative to the medical instrument. In such embodiments, the interface 600 can convey uncertainty via the anatomical representation 602, e.g., by altering the visual depiction of anatomic landmarks, passageways, boundaries such as airway walls, target site, and/or other anatomic structures. For example, anatomic structures can be displayed with increasing transparency and/or fuzziness as the amount of uncertainty increases. As another example, the uncertainty in the location of the medical instrument can be propagated to the location of a target site (e.g., a lesion or other biopsy target), and the visual characteristics of the target site can be modified to represent the uncertainty in its relative location (e.g., the representation of the target site increases in size to convey more uncertainty). In yet another example, anatomic structures may be depicted with varying colors, patterning, markings, and/or other indicators configured to visually convey the degree of uncertainty to the operator.

Referring back to FIG. 1, although the steps of the method 100 are discussed and illustrated in a particular order, a person of ordinary skill in the relevant art will recognize that the method 100 can be altered and still remain within these and other embodiments of the present technology. In other embodiments, for example, the method 100 can be performed in a different order, e.g., any of the steps of the method 100 can be performed before, during, and/or after any of the other steps of the method 100. For example, step 150 can be performed concurrently with steps 130 and 140. Additionally, one or more steps of the method 100 illustrated in FIG. 1 can be omitted (e.g., step 135, step 150). Optionally, one or more steps of the method 100 can be repeated (e.g., some or all of steps 120-150).

Figure 7:
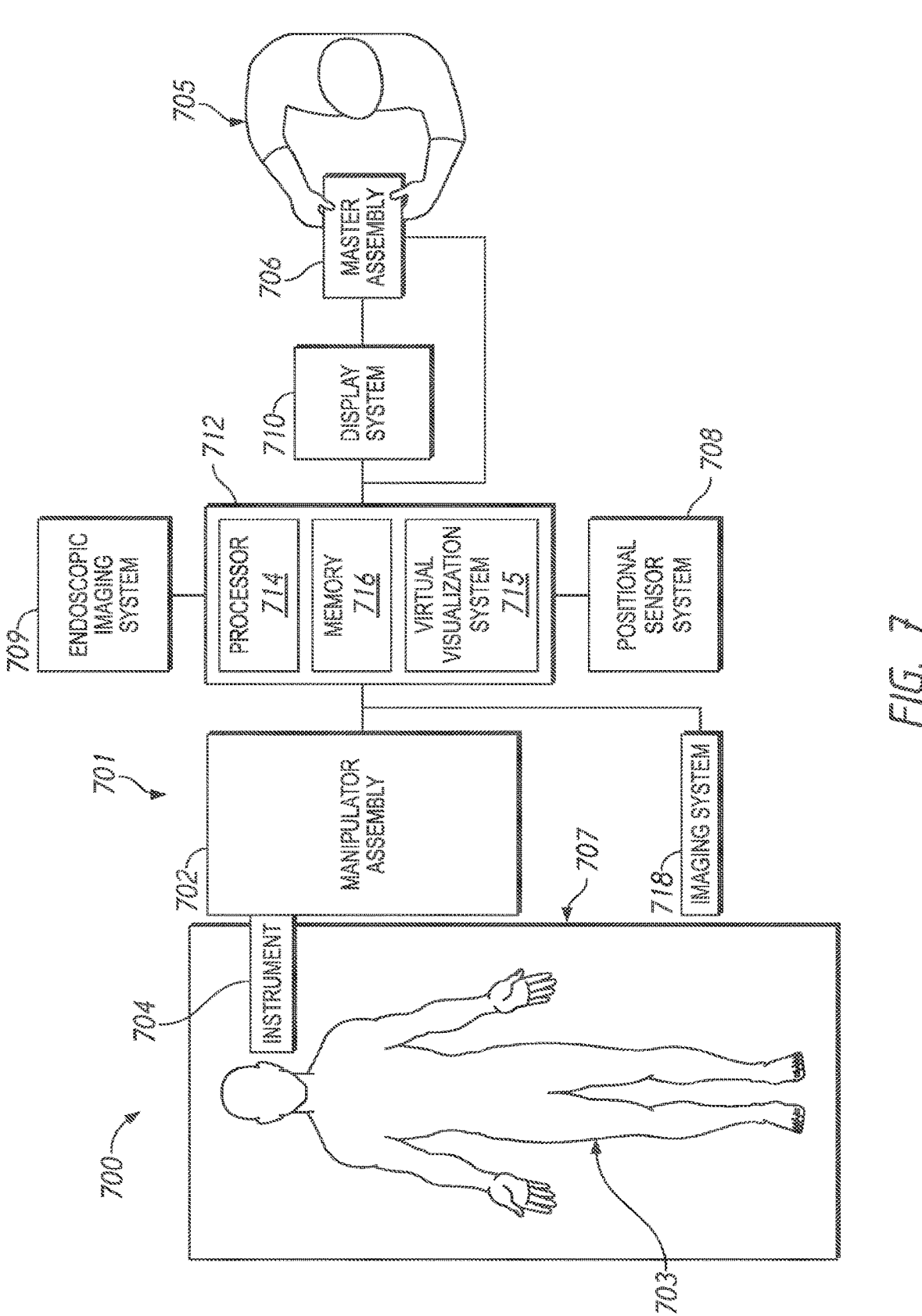
FIG. 7 is a schematic representation of a robotic or teleoperated medical system configured in accordance with various embodiments of the present technology.

B. Embodiments of Robotic or Teleoperated Medical Systems and Associated Devices, Systems, and Methods FIG. 7 is a schematic representation of a robotic or teleoperated medical system 700 ("medical system 700") configured in accordance with various embodiments of the present technology. The medical system 700 can be used with any of the procedures or methods described above with respect to FIGS. 1-6. For example, the medical system 700 can be used to monitor localization state of a medical instrument, as previously discussed. As shown, the medical system 700 includes a manipulator assembly 702, a medical instrument system 704, a master assembly 706, and a control system 712. The manipulator assembly 702 supports the medical instrument system 704 and drives the medical instrument system 704 at the direction of the master assembly 706 and/or the control system 712 to perform various medical procedures on a patient 703 positioned on a table 707 in a surgical environment 701. In this regard, the master assembly 706 generally includes one or more control devices that can be operated by an operator 705 (e.g., a physician) to control the manipulator assembly 702. Additionally, or alternatively, the control system 712 includes a computer processor 714 and at least one memory 716 for effecting control between the medical instrument system 704, the master assembly 706, and/or other components of the medical system 700. The control system 712 can also include programmed instructions (e.g., a non-transitory computer-readable medium storing the instructions) to implement any one or more of the methods described herein, including instructions for providing information to a display system 710 and/or processing data for registration of the medical instrument system 704 with an anatomical model of the patient 703 (as described in greater detail below). The manipulator assembly 702 can be a teleoperated, a non-teleoperated, or a hybrid teleoperated and non-teleoperated assembly. Thus, all or a portion of the master assembly 706 and/or all or a portion of the control system 712 can be positioned inside or outside of the surgical environment 701.

To aid the operator 705 in controlling the manipulator assembly 702 and/or the medical instrument system 704 during an image-guided medical procedure, the medical system 700 may further include a positional sensor system 708, an endoscopic imaging system 709, an imaging system 718, and/or a virtual visualization system 715. In some embodiments, the positional sensor system 708 includes a location sensor system (e.g., an electromagnetic (EM) sensor system) and/or a shape sensor system for capturing positional sensor data (e.g., position, orientation, speed, velocity, pose, shape, etc.) of the medical instrument system 704. In these and other embodiments, the endoscopic imaging system 709 includes one or more image capture devices (not shown) that record endoscopic image data that includes concurrent or real-time images (e.g., video, still images, etc.) of patient anatomy. Images captured by the endoscopic imaging system 709 may be, for example, two or three-dimensional images of patient anatomy captured by an image capture device positioned within the patient 703, and are referred to hereinafter as "real navigational images."

In some embodiments, the medical instrument system 704 may include components of the positional sensor system 708 and/or components of the endoscopic imaging system 709. For example, components of the positional sensor system 708 and/or components of the endoscopic imaging system 709 can be integrally or removably coupled to the medical instrument system 704. Additionally, or alternatively, the endoscopic imaging system 709 can include a separate endoscope (not shown) attached to a separate manipulator assembly (not shown) that can be used in conjunction with the medical instrument system 704 to image patient anatomy. The positional sensor system 708 and/or the endoscopic imaging system 709 may be implemented as hardware, firmware, software, or a combination thereof that interact with or are otherwise executed by one or more computer processors, such as the computer processor(s) 714 of the control system 712.

The imaging system 718 of the medical system 700 may be arranged in the surgical environment 701 near the patient 703 to obtain real-time and/or near real-time images of the patient 703 before, during, and/or after a medical procedure. In some embodiments, the imaging system 718 includes a mobile C-arm cone-beam CT imaging system for generating three-dimensional images. For example, the imaging system 718 can include a DynaCT imaging system from Siemens Corporation, or another suitable imaging system. In these and other embodiments, the imaging system 718 can include other imaging technologies, including MRI, fluoroscopy, thermography, ultrasound, OCT, thermal imaging, impedance imaging, laser imaging, nanotube X-ray imaging, and/or the like.

The virtual visualization system 715 of the control system 712 provides navigation and/or anatomy-interaction assistance to the operator 705 when controlling the medical instrument system 704 during an image-guided medical procedure. As described in greater detail below, virtual navigation using the virtual visualization system 715 can be based, at least in part, upon reference to an acquired pre-operative or intra-operative dataset (e.g., based, at least in part, upon reference to data generated by the positional sensor system 708, the endoscopic imaging system 709, and/or the imaging system 718) of anatomic passageways of the patient 703. In some implementations, for example, the virtual visualization system 715 processes preoperative and/or intraoperative image data of an anatomic region of the patient 703 captured by the imaging system 718 to generate an anatomic model (not shown) of the anatomic region. The virtual visualization system 715 then registers the anatomic model to positional sensor data generated by the positional sensor system 708 and/or to endoscopic image data generated by the endoscopic imaging system 709 to (i) map the tracked position, orientation, pose, shape, and/or movement of the medical instrument system 704 within the anatomic region to a correct position within the anatomic model, and/or (ii) determine a virtual navigational image of virtual patient anatomy of the anatomic region from a viewpoint of the medical instrument system 704 at a location within the anatomic model corresponding to a location of the medical instrument system 704 within the patient 703.

The display system 710 can display various images or representations of patient anatomy and/or of the medical instrument system 704 that are generated by the positional sensor system 708, by the endoscopic imaging system 709, by the imaging system 718, and/or by the virtual visualization system 715. In some embodiments, the display system 710 and/or the master assembly 706 may be oriented so the operator 705 can control the manipulator assembly 702, the medical instrument system 704, the master assembly 706, and/or the control system 712 with the perception of telepresence.

As discussed above, the manipulator assembly 702 drives the medical instrument system 704 at the direction of the master assembly 706 and/or the control system 712. In this regard, the manipulator assembly 702 can include select degrees of freedom of motion that may be motorized and/or teleoperated and select degrees of freedom of motion that may be non-motorized and/or non-teleoperated. For example, the manipulator assembly 702 can include a plurality of actuators or motors (not shown) that drive inputs on the medical instrument system 704 in response to commands received from the control system 712. The actuators can include drive systems (not shown) that, when coupled to the medical instrument system 704, can advance the medical instrument system 704 into a naturally or surgically created anatomic orifice. Other drive systems may move a distal portion (not shown) of the medical instrument system 704 in multiple degrees of freedom, which may include three degrees of linear motion (e.g., linear motion along the X, Y, Z Cartesian axes) and three degrees of rotational motion (e.g., rotation about the X, Y, Z Cartesian axes). Additionally, or alternatively, the actuators can be used to actuate an articulable end effector of the medical instrument system 704 (e.g., for grasping tissue in the jaws of a biopsy device and/or the like).

Figure 8:
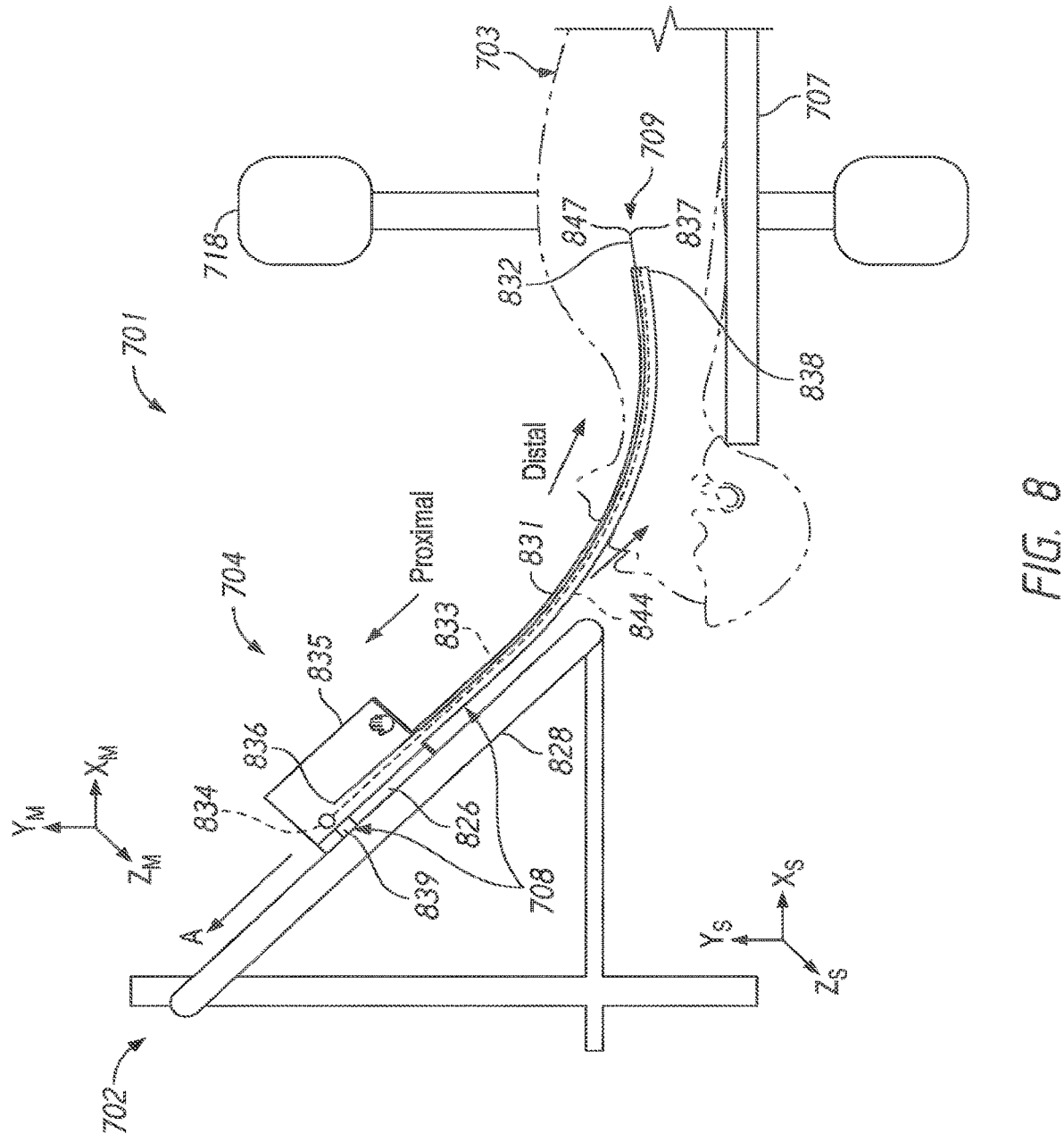
FIG. 8 is a schematic representation of a manipulator assembly, a medical instrument system, and an imaging system configured in accordance with various embodiments of the present technology.

FIG. 8 is a schematic representation of the manipulator assembly 702, the medical instrument system 704, and the imaging system 718 of FIG. 7 within the surgical environment 701 and configured in accordance with various embodiments of the present technology. As shown in FIG. 8, the surgical environment 701 has a surgical frame of reference (XS, YS, ZS) in which the patient 703 is positioned on the table 707, and the medical instrument system 704 has a medical instrument frame of reference (XM, YM, ZM) within the surgical environment 701. During the medical procedure, the patient 703 may be stationary within the surgical environment 701 in the sense that gross patient movement can be limited by sedation, restraint, and/or other means. In these and other embodiments, cyclic anatomic motion of the patient 703, including respiration and cardiac motion, may continue unless the patient 703 is asked to hold his or her breath to temporarily suspend respiratory motion.

The manipulator assembly 702 includes an instrument carriage 826 mounted to an insertion stage 828. In the illustrated embodiment, the insertion stage 828 is linear, while in other embodiments, the insertion stage 828 is curved or has a combination of curved and linear sections. In some embodiments, the insertion stage 828 is fixed within the surgical environment 701. Alternatively, the insertion stage 828 can be movable within the surgical environment 701 but have a known location (e.g., via a tracking sensor (not shown) or other tracking device) within the surgical environment 701. In these alternatives, the medical instrument frame of reference (XM, YM, ZM) is fixed or otherwise known relative to the surgical frame of reference (XS, YS, ZS).

The medical instrument system 704 of FIG. 8 includes an elongate device 831, a medical instrument 832, an instrument body 835, at least a portion of the positional sensor system 708, and at least a portion of the endoscopic imaging system 709. In some embodiments, the elongate device 831 is a flexible catheter or other biomedical device that defines a channel or lumen 844. The channel 844 can be sized and shaped to receive the medical instrument 832 (e.g., via a proximal end 836 of the elongate device 831 and/or an instrument port (not shown)) and facilitate delivery of the medical instrument 832 to a distal portion 838 of the elongate device 831. The elongate device 831 is coupled to the instrument body 835, which in turn is coupled and fixed relative to the instrument carriage 826 of the manipulator assembly 702.

In operation, the manipulator assembly 702 can control insertion motion (e.g., proximal and/or distal motion along an axis A) of the elongate device 831 into the patient 703 via a natural or surgically created anatomic orifice of the patient 703 to facilitate navigation of the elongate device 831 through anatomic passageways of an anatomic region of the patient 703 and/or to facilitate delivery of a distal portion 838 of the elongate device 831 to or near a target location within the patient 703. For example, the instrument carriage 826 and/or the insertion stage 828 may include actuators (not shown), such as servomotors, that facilitate control over motion of the instrument carriage 826 along the insertion stage 828. Additionally, or alternatively, the manipulator assembly 702 in some embodiments can control motion of the distal portion 838 of the elongate device 831 in multiple directions, including yaw, pitch, and roll rotational directions (e.g., to navigate patient anatomy). To this end, the elongate device 831 may house or include cables, linkages, and/or other steering controls (not shown) that the manipulator assembly 702 can use to controllably bend the distal portion 838 of the elongate device 831. For example, the elongate device 831 can house at least four cables that can be used by the manipulator assembly 702 to provide (i) independent "up-down" steering to control a pitch of the distal portion 838 of the elongate device 831 and (ii) independent "left-right" steering of the elongate device 831 to control a yaw of the distal portion 838 of the elongate device 831.

The medical instrument 832 of the medical instrument system 704 can be used for medical procedures, such as for survey of anatomic passageways, surgery, biopsy, ablation, illumination, irrigation, and/or suction. Thus, the medical instrument 832 can include image capture probes, biopsy instruments, laser ablation fibers, and/or other surgical, diagnostic, and/or therapeutic tools. For example, the medical instrument 832 can include an endoscope or other biomedical device having one or more image capture devices 847 positioned at a distal portion 837 of and/or at other locations along the medical instrument 832. In these embodiments, an image capture device 847 can capture one or more real navigational images or video (e.g., a sequence of one or more real navigational image frames) of anatomic passageways and/or other real patient anatomy while the medical instrument 832 is within an anatomic region of the patient 703.

As discussed above, the medical instrument 832 can be deployed into and/or be delivered to a target location within the patient 703 via the channel 844 defined by the elongate device 831. In embodiments in which the medical instrument 832 includes an endoscope or other biomedical device having an image capture device 847 at its distal portion 837, the image capture device 847 can be advanced to the distal portion 838 of the elongate device 831 before, during, and/or after the manipulator assembly 702 navigates the distal portion 838 of the elongate device 831 to a target location within the patient 703. In these embodiments, the medical instrument 832 can be used as a survey instrument to capture real navigational images of anatomic passageways and/or other real patient anatomy, and/or to aid an operator (not shown) to navigate the distal portion 838 of the elongate device 831 through anatomic passageways to the target location.

As another example, after the manipulator assembly 702 positions the distal portion 838 of the elongate device 831 proximate a target location within the patient 703, the medical instrument 832 can be advanced beyond the distal portion 838 of the elongate device 831 to perform a medical procedure at the target location. Continuing with this example, after all or a portion of the medical procedure at the target location is complete, the medical instrument 832 can be retracted back into the elongate device 831 and, additionally or alternatively, be removed from the proximal end 836 of the elongate device 831 or from another instrument port (not shown) along the elongate device 831.

As shown in FIG. 8, the positional sensor system 708 of the medical instrument system 704 includes a shape sensor 833 and a position measuring device 839. In these and other embodiments, the positional sensor system 708 can include other position sensors (e.g., accelerometers, rotary encoders, etc.) in addition to or in lieu of the shape sensor 833 and/or the position measuring device 839.

The shape sensor 833 of the positional sensor system 708 includes an optical fiber extending within and aligned with the elongate device 831. In one embodiment, the optical fiber of the shape sensor 833 has a diameter of approximately 200 μm. In other embodiments, the diameter of the optical fiber may be larger or smaller. The optical fiber of the shape sensor 833 forms a fiber optic bend sensor that is used to determine a shape, orientation, and/or pose of the elongate device 831. In some embodiments, optical fibers having Fiber Bragg Gratings (FBGs) can be used to provide strain measurements in structures in one or more dimensions. Various systems and methods for monitoring the shape and relative position of an optical fiber in three dimensions are described in further detail in U.S. Patent Application Publication No. 2006/0013523 (filed Jul. 13, 2005) (disclosing fiber optic position and shape sensing device and method relating thereto); U.S. Pat. No. 7,781,724 (filed on Sep. 26, 2006) (disclosing fiber-optic position and shape sensing device and method relating thereto); U.S. Pat. No. 7,772,541 (filed on Mar. 12, 2008) (disclosing fiber-optic position and/or shape sensing based on Rayleigh scatter); and U.S. Pat. No. 6,389,187 (filed on Jun. 17, 1998) (disclosing optical fiber bend sensors), which are all incorporated by reference herein in their entireties. In these and other embodiments, sensors of the present technology may employ other suitable strain sensing techniques, such as Rayleigh scattering, Raman scattering, Brillouin scattering, and Fluorescence scattering. In these and still other embodiments, the shape of the elongate device 831 may be determined using other techniques. For example, a history of the pose of the distal portion 838 of the elongate device 831 can be used to reconstruct the shape of elongate device 831 over an interval of time.

In some embodiments, the shape sensor 833 is fixed at a proximal point 834 on the instrument body 835 of the medical instrument system 704. In operation, for example, the shape sensor 833 measures a shape in the medical instrument reference frame (XM, YM, ZM) from the proximal point 834 to another point along the optical fiber, such as the distal portion 838 of the elongate device 831. The proximal point 834 of the shape sensor 833 may be movable along with instrument body 835 but the location of proximal point 834 may be known (e.g., via a tracking sensor (not shown) or other tracking device).

The position measuring device 839 of the positional sensor system 708 provides information about the position of the instrument body 835 as it moves along the insertion axis A on the insertion stage 828 of the manipulator assembly 702. In some embodiments, the position measuring device 839 includes resolvers, encoders, potentiometers, and/or other sensors that determine the rotation and/or orientation of actuators (not shown) controlling the motion of the instrument carriage 826 of the manipulator assembly 702 and, consequently, the motion of the instrument body 835 of the medical instrument system 704.

Figures 9, 10, 11, 12:
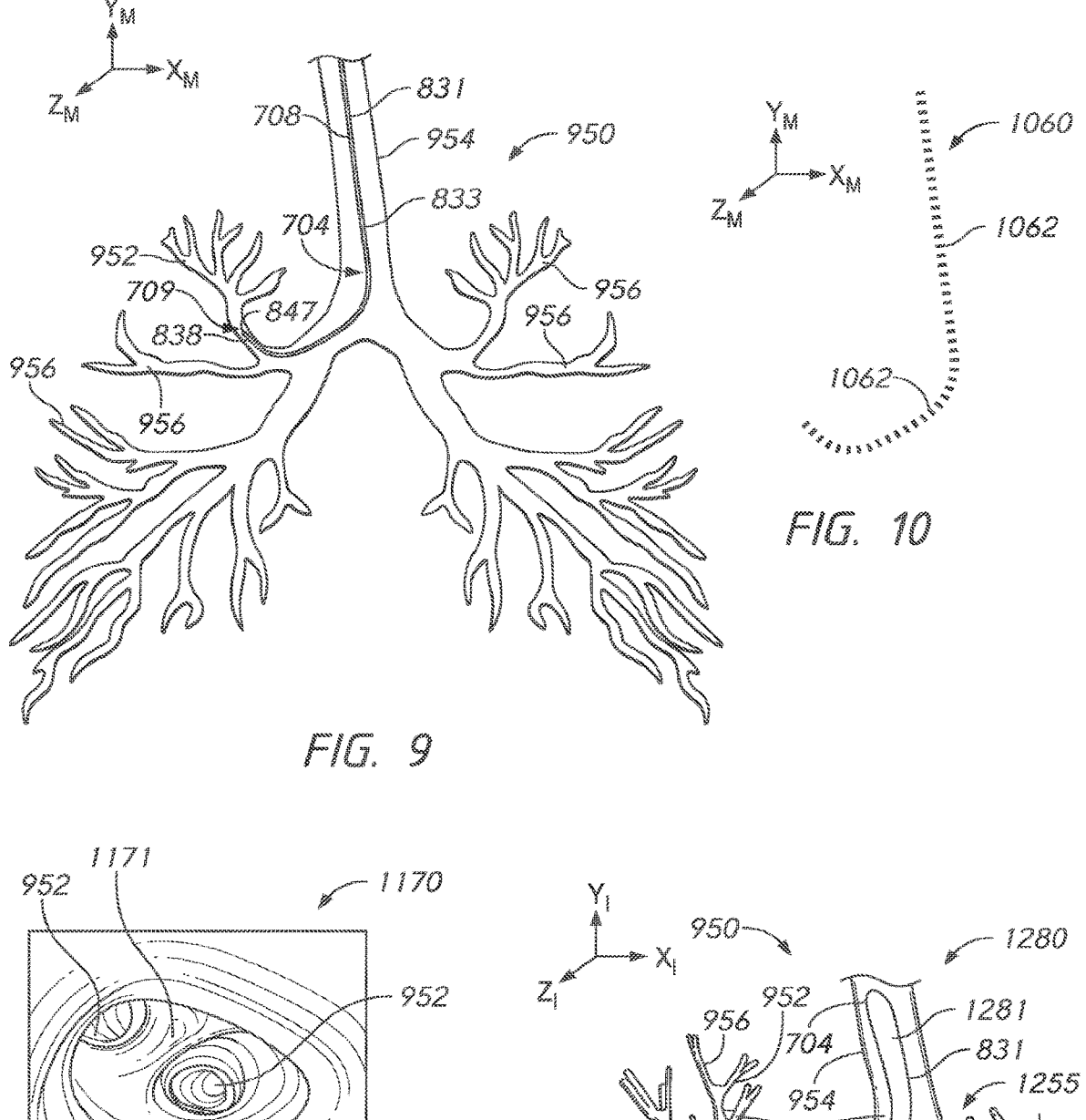
FIG. 9 is a schematic representation of a portion of the medical instrument system of FIG. 8 extended within an anatomic region of a patient in accordance with various embodiments of the present technology.
FIG. 10 illustrates a plurality of coordinate points forming a point cloud representing a shape of the portion of the medical instrument system of FIG. 9 configured in accordance with various embodiments of the present technology.
FIG. 11 illustrates a real navigational image of real patient anatomy from a viewpoint of the portion of the medical instrument system of FIG. 9 extended within the anatomic region of FIG. 9 in accordance with various embodiments of the present technology.
FIG. 12 illustrates an intraoperative image of a portion of the anatomic region of FIG. 9 while the portion of the medical instrument system of FIG. 9 is extended within the anatomic region in accordance with various embodiments of the present technology.

FIG. 9 is a schematic representation of a portion of the medical instrument system 704 of FIG. 8 extended within an anatomic region 950 (e.g., human lungs) of the patient 703 in accordance with various embodiments of the present technology. In particular, FIG. 9 illustrates the elongate device 831 of the medical instrument system 704 extending within branched anatomic passageways 952 of the anatomic region 950. The anatomic passageways 952 include a trachea 954 and a plurality of bronchial tubes 956.

As shown in FIG. 9, the elongate device 831 has a position, orientation, pose, and shape within the anatomic region 950, all or a portion of which (in addition to or in lieu of movement, such as speed or velocity) can be captured as positional sensor data by the positional sensor system 708 of FIGS. 7 and 8 (e.g., by the shape sensor 833 and/or the position measuring device 839 (FIG. 8)) to survey the anatomic passageways 952 of the anatomic region 950. In particular, the positional sensor system 708 can survey the anatomic passageways 952 by gathering positional sensor data of the medical instrument system 704 within the anatomic region 950 in the medical instrument frame of reference (XM, YM, ZM). The positional sensor data may at least in part be recorded as a set of two-dimensional or three-dimensional coordinate points. In the example of the anatomic region 950 being human lungs, the coordinate points may represent the locations of the distal portion 838 of the elongate device 831 and/or of other portions of the elongate device 831 while the elongate device 831 is advanced through the trachea 954 and the bronchial tubes 956. In these and other embodiments, the collection of coordinate points may represent the shape(s) of the elongate device 831 while the elongate device 831 is advanced through the anatomic region 950. In these and still other embodiments, the coordinate points may represent positional data of other portions (e.g., the medical instrument 832 (FIG. 8)) of the medical instrument system 704.

The coordinate points may together form a point cloud. For example, FIG. 10 illustrates a plurality of coordinate points 1062 forming a point cloud 1060 representing a shape of the elongate device 831 of FIG. 9 while the elongate device 831 is within the anatomic region 950 (FIG. 9) in accordance with various embodiments of the present technology. In particular, the point cloud 1060 of FIG. 10 is generated from the union of all or a subset of the coordinate points 1062 recorded by the positional sensor system 708 (FIG. 8) while the elongate device 831 is in the stationary position illustrated in FIG. 9.

In some embodiments, a point cloud (e.g., the point cloud 1060) can include the union of all or a subset of coordinate points recorded by the positional sensor system 708 during an image capture period that spans multiple shapes, positions, orientations, and/or poses of the elongate device 831 within the anatomic region 950. In these embodiments, the point cloud can include coordinate points captured by the positional sensor system 708 that represent multiple shapes of the elongate device 831 while the elongate device 831 is advanced or moved through patient anatomy during the image capture period. Additionally, or alternatively, because the configuration, including shape and location, of the elongate device 831 within the patient 703 may change during the image capture period due to anatomical motion, the point cloud in some embodiments can comprise a plurality of coordinate points 1062 captured by the positional sensor system 708 that represent the shapes of the elongate device 831 as the elongate device 831 passively moves within the patient 703. As described in greater detail below, a point cloud of coordinate points captured by the positional sensor system 708 can be registered to different models or datasets of patient anatomy.

Referring again to FIG. 8, the endoscopic imaging system 709 of the medical instrument system 704 includes one or more image capture devices 847 configured to capture one or more real navigational images of real patient anatomy (e.g., the anatomic passageways 952 of FIG. 9) while the elongate device 831 and/or the medical instrument 832 is within an anatomic region (e.g., the anatomic region 950 of FIG. 9) of the patient 703. For example, the endoscopic imaging system 709 can include an image capture device 847 positioned at the distal portion 837 of the medical instrument 832. In these and other embodiments, the endoscopic imaging system 709 can include one or more image capture devices (not shown) positioned at other locations along the medical instrument 832 and/or along the elongate device 831 (e.g., at the distal portion 838 of the elongate device 831).

In the embodiment illustrated in FIG. 9, the image capture device 847 of the medical instrument 832 (FIG. 8) is advanced to and positioned at the distal portion 838 of the elongate device 831. In this embodiment, the image capture device 847 can survey the anatomic passageways 952 by capturing real navigational images of the anatomic passageways 952 while the elongate device 831 is navigated through the trachea 954 and the bronchial tubes 956 of the anatomic region 950.

FIG. 11 is an example of a real navigational image 1170 (e.g., a still image, an image frame of a video, etc.) of patient anatomy of the anatomic region 950 of FIG. 9 (such as one of the anatomic passageways 952) captured via the image capture device 847 (FIG. 9). As shown, the real navigational image 1170 shows a branching point or carina 1171 of two anatomic passageways 952 within the anatomic region 950 from a viewpoint of the medical instrument 832 (FIG. 8). In this example, because the image capture device 847 is positioned at the distal portions 837 and 838 of the medical instrument 832 and the elongate device 831 (FIG. 9), respectively, the viewpoint of the real navigational image

1170 is from the distal portion 837 of the medical instrument 832 such that the medical instrument 832 and the elongate device 831 are not visible within the real navigational image 1170. In other embodiments, the image capture device 847 can be positioned at another location along the medical instrument 832 and/or along the elongate device 831 (FIGS. 8 and 9). In these embodiments, the endoscopic imaging system 119 (FIG. 8) can capture real navigational images from a corresponding viewpoint of the medical instrument 832 and/or of the elongate device 831. A portion of the medical instrument 832 and/or of the elongate device 831 may be visible within these real navigational images depending on the positions of the medical instrument 832 and the elongate device 831 relative to one another.

Referring again to FIG. 8, the real navigational images captured by the endoscopic imaging system 709 can facilitate navigation of the distal portion 838 of the elongate device 831 through patient anatomy (e.g., through the anatomic passageways 952 of FIG. 9) and/or delivery of the distal portion 838 of the elongate device 831 to a target location within the patient 703. In these and other embodiments, the real navigational images captured by the endoscopic imaging system 709 can facilitate (i) navigation of the distal portion 837 of the medical instrument 832 beyond the distal portion 838 of the elongate device 831, (ii) delivery of the distal portion 837 of the medical instrument 832 to a target location within the patient 703, and/or (iii) visualization of patient anatomy during a medical procedure. In some embodiments, each real navigational image captured by the endoscopic imaging system 709 can be associated with a time stamp and/or a position recorded in the medical instrument frame of reference (XM, YM, ZM). The real navigational images captured by the endoscopic imaging system 709 can optionally be used to improve a registration between a point cloud of coordinate points (e.g., the point cloud 1060 of FIG. 10) generated by the positional sensor system 708 and image data captured by the imaging system 718.

As shown in FIG. 8, the imaging system 718 is arranged near the patient 703 to obtain three-dimensional images of the patient 703 (e.g., of the anatomic region 950 of FIG. 9). In some embodiments, the imaging system 718 includes one or more imaging technologies, including CT, MRI, fluoroscopy, thermography, ultrasound, OCT, thermal imaging, impedance imaging, laser imaging, nanotube X-ray imaging, and/or the like. The imaging system 718 is configured to generate image data of patient anatomy before, during, and/or after the elongate device 831 is extended within the patient 703. Thus, the imaging system 718 can be configured to capture preoperative, intraoperative, and/or postoperative three-dimensional images of patient anatomy. In these and other embodiments, the imaging system 718 may provide real-time or near real-time images of patient anatomy.

FIG. 12 illustrates an example of intraoperative image data 1280 of a portion 1255 of the anatomic region 950 of FIG. 9 captured during an image capture period by the imaging system 718 (FIG. 8) while the elongate device 831 of the medical instrument system 704 is extended within the anatomic region 950. As shown, the image data 1280 includes graphical elements 1281 representing the elongate device 831 and graphical elements 1282 representing the anatomic passageways 952 of the anatomic region 950.

All or a portion of the graphical elements 1281 and 1282 of the image data 1280 can be segmented and/or filtered to generate a virtual, three-dimensional model of the anatomic passageways 952 within the portion 1255 of the anatomic region 950 (with or without the medical instrument system 704). In some embodiments, the graphical elements 1281 and 1282 can additionally or alternatively be segmented and/or filtered to generate an image point cloud (not shown) of the medical instrument system 704 based, at least in part, on images captured by the imaging system 128 (FIG. 8) while the medical instrument system 704 is within the anatomic region 950. During the segmentation process, pixels or voxels generated from the image data 1280 may be partitioned into segments or elements or be tagged to indicate that they share certain characteristics or computed properties such as color, density, intensity, and texture. The segments or elements may then be converted to an anatomic model and/or to an image point cloud of the medical instrument system 704. Additionally, or alternatively, the segments or elements can be used to locate (e.g., calculate) and/or define a center line or other points running along the anatomic passageways 952. The generated anatomic model and/or the image point cloud may be two or three-dimensional and may be generated in an image reference frame (XI, YI, ZI).

As discussed above with respect to FIG. 7, the display system 710 (FIG. 7) of the medical system 700 (FIG. 7) can display various images or representations of patient anatomy and/or of the medical instrument system 704 based, at least in part, on data captured and/or generated by the positional sensor system 708, by the endoscopic imaging system 709, by the imaging system 718, and/or by the virtual visualization system 715. In various implementations, the images and/or representations can be utilized by the system to aid the operator 705 (FIG. 7) in conducting an image-guided medical procedure.

Figure 13:
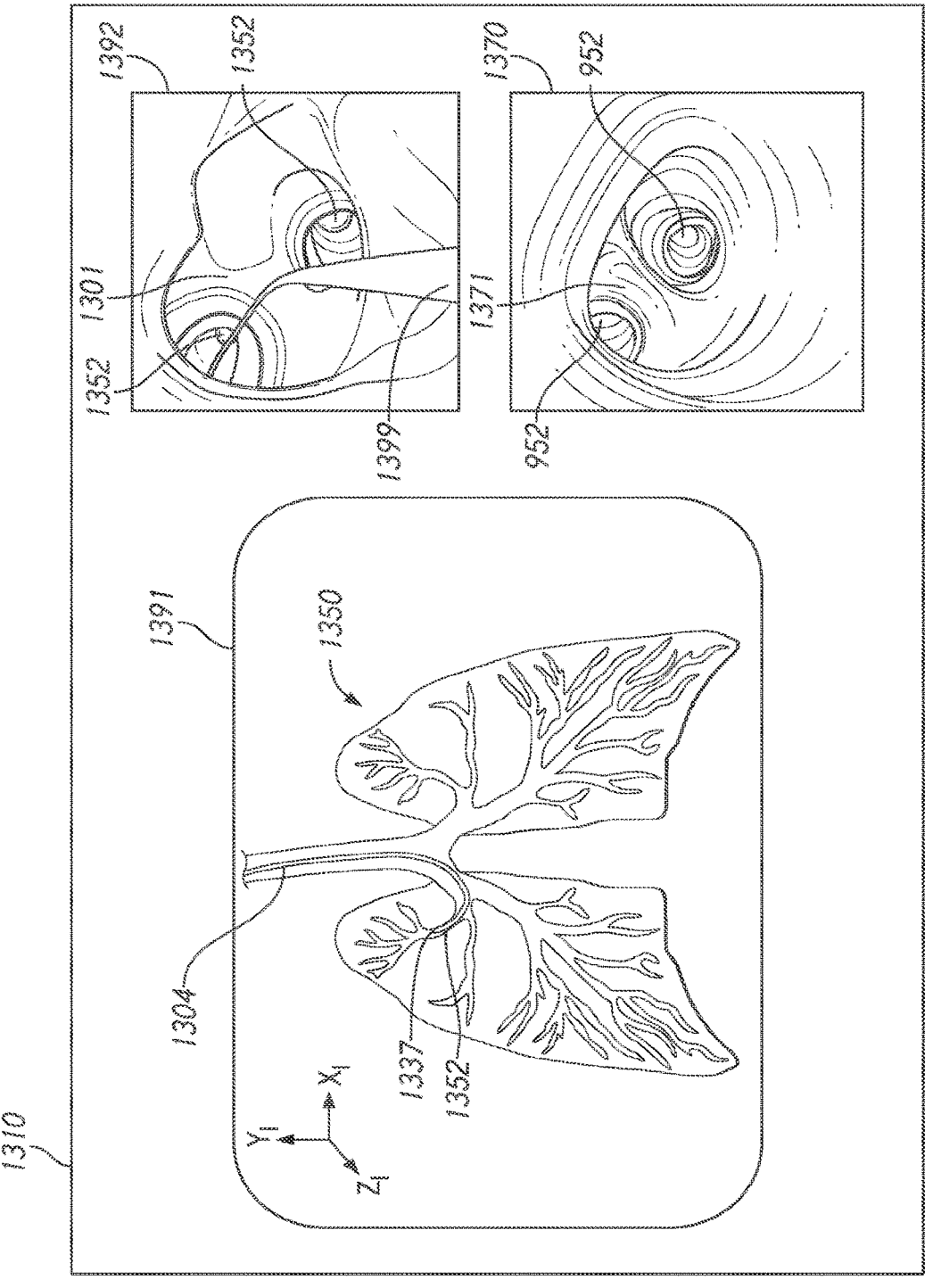
FIG. 13 is a schematic representation of a display of a display system displaying a composite virtual navigational image in which the medical instrument system of FIGS. 8 and 9 is registered to an anatomic model of the anatomic region of FIG. 9, a virtual navigational image of virtual patient anatomy, and a real navigational image of real patient anatomy within the anatomic region in accordance with various embodiments of the present technology.

FIG. 13 is a schematic representation of an example display 1310 produced by the display system 710 (FIG. 7) in accordance with various embodiments of the present technology. As shown, the display 1310 includes a real navigational image 1370, a composite virtual navigational image 1391 (also referred to as a "composite virtual image 1391"), and a virtual navigational image 1392. The real navigational image 1370 can be substantially the same as the real navigational image 1170 of FIG. 11. Thus, for example, the real navigational image 1370 can be captured by the endoscopic imaging system 709 (FIG. 8) and provided to the display system 710 (FIG. 7) to be presented on the display 1310 in real-time or near real-time. In the illustrated embodiment, the real navigational image 1370 illustrates real patient anatomy (e.g., a carina 1371 marking a branching point of two anatomic passageways 952) from a viewpoint oriented distally away from the distal portion 837 of the medical instrument 832 (FIG. 8).

The composite virtual image 1391 of FIG. 13 is displayed in the image reference frame (XI, YI, ZI) and includes an anatomic model 1350 generated from image data of the anatomic region 950 of FIG. 9 captured by the imaging system 718 (FIG. 8). The anatomic model 1350 is registered (i.e., dynamically referenced) with a point cloud of coordinate points (e.g., the point cloud 1060 of FIG. 10) generated by the positional sensor system 708 (FIG. 8) to display a representation 1304 within the anatomic model 1350 of the tracked position, shape, pose, orientation, and/or movement of the medical instrument system 704 (e.g., of the elongate device 831 of FIG. 8) within the patient 703 (FIG. 8). In some embodiments, the composite virtual image 1391 is generated by the virtual visualization system 715 (FIG. 7) of the control system 712 (FIG. 7). Generating the composite virtual image 1391 involves registering the image reference frame (XI, YI, ZI) with the surgical reference frame (XS, YS, ZS) and/or to the medical instrument reference frame (XM, YM, ZM). This registration may rotate, translate, or otherwise manipulate by rigid and/or non-rigid transforms coordinate points of the point cloud (e.g., the coordinate points 1062 of the point cloud 1060 of FIG. 10) captured by the positional sensor system 708 to align the coordinate points with the anatomic model 1350. The registration between the image and surgical/instrument frames of reference may be achieved, for example, by using a point-based ICP technique, as described in U.S. Provisional Pat. App. Nos. 72/205,440 and No. 72/205,433, which are both incorporated by reference herein in their entireties. In other embodiments, the registration can be achieved using another point cloud registration technique.

Based, at least in part, on the registration, the virtual visualization system 715 can additionally or alternatively generate virtual navigational images (e.g., the virtual navigational image 1392 of FIG. 13) that include a virtual depiction of patient anatomy from a viewpoint of a virtual camera on the representation 1304 of the medical instrument system 704 (FIG. 9) within the anatomic model 1350. In the embodiment illustrated in FIG. 13, the virtual camera of the virtual navigational image 1392 is positioned at a distal portion 1337 of the representation 1304 such that (i) the virtual viewpoint of the virtual navigational image 1392 is directed distally away from the distal portion 1337 of the representation 1304 and (ii) the representation 1304 is not visible within the virtual navigational image 1392. In other embodiments, the virtual visualization system 715 can position the virtual camera (a) at another location along the representation 1304 and/or (b) in a different orientation such that the virtual navigational image 1392 has a corresponding virtual viewpoint. In some embodiments, depending on the position and orientation of the virtual camera and on the positions of the elongate device 831 and the medical instrument 832 relative to one another within the patient 703, the virtual visualization system 715 can render a virtual representation (not shown) of at least a portion of the elongate device 831 and/or of the medical instrument 832 into the virtual navigational image 1392.

In some embodiments, the virtual visualization system 715 can place the virtual camera within the anatomic model 1350 at a position and orientation corresponding to the position and orientation of the image capture device 847 within the patient 703 (FIG. 8). As further shown in FIG. 13, the virtual navigational image 1392 illustrates virtual anatomy, such as a carina 1301 marking a branching point of two anatomic passageways 1352 of the anatomic model 1350, from substantially the same location at which the real navigational image 1370 is captured by the image capture device 847 (FIG. 8). Thus, the virtual navigational image 1392 provides a rendered estimation of patient anatomy visible to the image capture device 847 at a given location within the anatomic region 950 of FIG. 9. Because the virtual navigational image 1392 is based, at least in part, on the registration of a point cloud generated by the positional sensor system 708 and image data captured by the imaging system 718, the correspondence between the virtual navigational image 1392 and the real navigational image 1370 provides insight regarding the accuracy of the registration and can be used to improve the registration. Furthermore, the real navigational images (e.g., the real navigational image 1370) captured by the endoscopic imaging system 709 (FIG. 8) can (a) provide information regarding the position and orientation of the medical instrument system 704 (FIG. 7) within the patient 703, (b) provide information regarding portions of an anatomic region actually visited by the medical instrument system, and/or (c) help identify patient anatomy (e.g., branching points of anatomic passageways) proximate the medical instrument system 704, any one or more of which can be used to improve the accuracy of the registration.

As further shown in FIG. 13, the virtual navigational image 1392 can optionally include a navigation path overlay 1399. In some embodiments, the navigation path overlay 1399 is used to aid an operator 705 (FIG. 7) to navigate the medical instrument system 704 (FIG. 7) through anatomic passageways of an anatomic region to a target location within a patient 703. For example, the navigation path overlay 1399 can illustrate a "best" path through an anatomic region for an operator 705 to follow to deliver the distal portions 837 and/or 838 of the medical instrument 832 and/or of the elongate device 831, respectively, to a target location within the patient 703. In some embodiments, the navigation path overlay 1399 can be aligned with a centerline of or another line along (e.g., the floor of) a corresponding anatomic passageway.

C. Conclusion

The systems and methods described herein can be provided in the form of tangible and non-transitory machine-readable medium or media (such as a hard disk drive, hardware memory, etc.) having instructions recorded thereon for execution by a processor or computer.

The set of instructions can include various commands that instruct the computer or processor to perform specific operations such as the methods and processes of the various embodiments described here. The set of instructions can be in the form of a software program or application. The computer storage media can include volatile and non-volatile media, and removable and non-removable media, for storage of information such as computer-readable instructions, data structures, program modules or other data. The computer storage media can include, but are not limited to, RAM, ROM, EPROM, EEPROM, flash memory or other solid-state memory technology, CD-ROM, DVD, or other optical storage, magnetic disk storage, or any other hardware medium which can be used to store desired information and that can be accessed by components of the system. Components of the system can communicate with each other via wired or wireless communication. The components can be separate from each other, or various combinations of components can be integrated together into a monitor or processor or contained within a workstation with standard computer hardware (for example, processors, circuitry, logic circuits, memory, and the like). The system can include processing devices such as microprocessors, microcontrollers, integrated circuits, control units, storage media, and other hardware.

Although many of the embodiments are described above in the context of navigating and performing medical procedures within lungs of a patient, other applications and other embodiments in addition to those described herein are within the scope of the present technology. For example, unless otherwise specified or made clear from context, the devices, systems, methods, and computer program products of the present technology can be used for various image-guided medical procedures, such as medical procedures performed on, in, or adjacent hollow patient anatomy, and, more specifically, in procedures for surveying, biopsying, ablating, or otherwise treating tissue within and/or proximal the hollow patient anatomy. Thus, for example, the systems, devices, methods, and computer program products of the present disclosure can be used in one or more medical procedures associated with other patient anatomy, such as the bladder, urinary tract, GI system, and/or heart of a patient.

This disclosure describes various instruments and portions of instruments in terms of their state in three-dimensional space. As used herein, the term "position" refers to the location of an object or a portion of an object in a three-dimensional space (e.g., three degrees of translational freedom along Cartesian x-, y-, and z-coordinates). As used herein, the term "orientation" refers to the rotational placement of an object or a portion of an object (three degrees of rotational freedom—e.g., roll, pitch, and yaw). As used herein, the term "pose" refers to the position of an object or a portion of an object in at least one degree of translational freedom and to the orientation of that object or portion of the object in at least one degree of rotational freedom (up to six total degrees of freedom). As used herein, the term "shape" refers to a set of poses, positions, or orientations measured along an object.

As used herein, the term "operator" shall be understood to include any type of personnel who may be performing or assisting a medical procedure and, thus, is inclusive of a physician, a surgeon, a doctor, a nurse, a medical technician, other personnel or user of the technology disclosed herein, and any combination thereof. Additionally, or alternatively, the term "patient" should be considered to include human and/or non-human (e.g., animal) patients upon which a medical procedure is being performed.

From the foregoing, it will be appreciated that specific embodiments of the technology have been described herein for purposes of illustration, but well-known structures and functions have not been shown or described in detail to avoid unnecessarily obscuring the description of the embodiments of the technology. To the extent any materials incorporated herein by reference conflict with the present disclosure, the present disclosure controls. Where the context permits, singular or plural terms can also include the plural or singular term, respectively. Moreover, unless the word "or" is expressly limited to mean only a single item exclusive from the other items in reference to a list of two or more items, then the use of "or" in such a list is to be interpreted as including (a) any single item in the list, (b) all of the items in the list, or (c) any combination of the items in the list. As used herein, the phrase "and/or" as in "A and/or B" refers to A alone, B alone, and both A and B. Where the context permits, singular or plural terms can also include the plural or singular term, respectively. Additionally, the terms "comprising," "including," "having" and "with" are used throughout to mean including at least the recited feature(s) such that any greater number of the same feature and/or additional types of other features are not precluded.

Furthermore, as used herein, the term "substantially" refers to the complete or nearly complete extent or degree of an action, characteristic, property, state, structure, item, or result. For example, an object that is "substantially" enclosed would mean that the object is either completely enclosed or nearly completely enclosed. The exact allowable degree of deviation from absolute completeness may in some cases depend on the specific context. However, generally speaking the nearness of completion will be so as to have the same overall result as if absolute and total completion were obtained. The use of "substantially" is equally applicable when used in a negative connotation to refer to the complete or near complete lack of an action, characteristic, property, state, structure, item, or result.

The above detailed descriptions of embodiments of the technology are not intended to be exhaustive or to limit the technology to the precise form disclosed above. Although specific embodiments of, and examples for, the technology are described above for illustrative purposes, various equivalent modifications are possible within the scope of the technology, as those skilled in the relevant art will recognize. For example, while steps are presented in a given order, alternative embodiments can perform steps in a different order. As another example, various components of the technology can be further divided into subcomponents, and/or various components and/or functions of the technology can be combined and/or integrated. Furthermore, although advantages associated with certain embodiments of the technology have been described in the context of those embodiments, other embodiments can also exhibit such advantages, and not all embodiments need necessarily exhibit such advantages to fall within the scope of the technology.

It should also be noted that other embodiments in addition to those disclosed herein are within the scope of the present technology. For example, embodiments of the present technology can have different configurations, components, and/or procedures in addition to those shown or described herein. Moreover, a person of ordinary skill in the art will understand that these and other embodiments can be without several of the configurations, components, and/or procedures shown or described herein without deviating from the present technology. Accordingly, the disclosure and associated technology can encompass other embodiments not expressly shown or described herein.

What is claimed is:

1. A system for performing a medical procedure within an anatomic region of a patient, the system comprising:
   a medical instrument configured to be inserted along a navigational path to a target location within the anatomic region, wherein the medical instrument includes an image capture device;
   a processor operably coupled to the image capture device; and
   a memory operably coupled to the processor and storing instructions that, when executed by the processor, cause the system to perform operations comprising:
      receiving a three-dimensional (3D) model of the anatomic region;
      determining a plurality of image capture locations for the image capture device within the anatomic region, wherein at least one of the plurality of image capture locations is offset from the navigational path to the target location;
      obtaining, from the image capture device, image data of an anatomic landmark within the anatomic region from the determined plurality of image capture locations, wherein at least some of the image data of the anatomic landmark is obtained from the at least one of the plurality of image capture locations that is offset from the navigational path to the target location;
      identifying, based on the image data, an association between the anatomic landmark and a corresponding model landmark in the 3D model;
      determining a localization state of the medical instrument based, at least in part, on the association between the anatomic landmark and the corresponding model landmark, the localization state including an estimated location of the medical instrument and an uncertainty parameter associated with the estimated location; and
   dynamically updating the localization state as the medical instrument traverses the anatomic region.

2. The system of claim 1 wherein obtaining the image data includes:
   monitoring location data associated with the image data obtained at the plurality of image capture locations; and
   based on the monitored location data, prompting collection of additional image data from at least one additional image capture location.

3. The system of claim 1 wherein identifying the association comprises:
   generating at least one two-dimensional (2D) virtual view of the model landmark; and
   comparing the image data to the at least one 2D virtual view.

4. The system of claim 1 wherein identifying the association comprises:
   generating, based on the image data, a 3D representation of the anatomic landmark; and
   comparing the 3D representation to a portion of the 3D model including the model landmark.

5. The system of claim 4 wherein the 3D representation is generated from the image data using one or more of the following: a shape from shading algorithm, a structure from motion algorithm, a single-shot depth estimation algorithm, or an end-to-end depth estimation algorithm.

6. The system of claim 1 wherein the 3D model represents a first portion of the anatomic region and the operations further comprise:
   detecting, based on the image data, that the medical instrument is within a second portion of the anatomic region, the second portion being different from the first portion;
   generating, based on the image data, a 3D representation of the second portion of the anatomic region; and
   adding the 3D representation to the 3D model.

7. The system of claim 1, further comprising a positional sensor configured to generate positional data of the medical instrument, wherein the localization state is determined based, at least in part, on the positional data.

8. The system of claim 1 wherein determining the localization state comprises:
   generating a plurality of state estimates for the medical instrument, each state estimate including a respective estimated location and a respective uncertainty parameter, wherein the state estimates include at least one state estimate generated from the image data; and
   combining the state estimates to determine the localization state.

9. The system of claim 8 wherein the plurality of state estimates include one or more state estimates generated from one or more of the following: positional data from a positional sensor, a registration between the 3D model and the anatomic region, control signals for the medical instrument, user input from an operator of the medical instrument, external image data generated by an external imaging device, or sensor data from at least one additional sensor.

10. The system of claim 1 wherein the localization state is determined using one or more of the following: a Kalman filter, a factor graph, or a particle filter.

11. The system of claim 1 wherein the localization state is determined based, at least partly, on one or more previous localization states of the medical instrument.

12. The system of claim 1 wherein the localization state is continuously updated at a rate of at least 30 times per second.

13. The system of claim 1 wherein the localization state is determined without performing an initial registration between the 3D model and the anatomic region.

14. The system of claim 1 wherein the operations further comprise outputting a graphical representation of the localization state to an operator, the graphical representation including a first visual indicator representing the estimated location and a second visual indicator representing the uncertainty parameter.

15. A non-transitory, computer-readable medium storing instructions thereon that, when executed by one or more processors of a computing system, cause the computing system to perform operations comprising:

receiving a three-dimensional (3D) model of an anatomic region;

determining a plurality of image capture locations for an image capture device carried by a medical instrument within the anatomic region, wherein at least one of the plurality of image capture locations is offset from a navigational path to a target location;

obtaining, from the image capture device, image data of an anatomic landmark within the anatomic region from the determined plurality of image capture locations, wherein at least some of the image data of the anatomic landmark is obtained from the at least one of the plurality of image capture locations that is offset from the navigational path to the target location;

identifying, based on the image data, an association between the anatomic landmark and a corresponding model landmark in the 3D model;

determining a localization state of the medical instrument based, at least in part, on the association between the anatomic landmark and the corresponding model landmark, the localization state including an estimated location of the medical instrument and an uncertainty parameter associated with the estimated location; and dynamically updating the localization state as the medical instrument traverses the anatomic region.

16. The non-transitory, computer-readable medium of claim 15 wherein determining the localization state comprises:

generating a plurality of state estimates for the medical instrument, each state estimate including a respective estimated location and a respective uncertainty parameter, wherein the state estimates include at least one state estimate generated from the image data; and combining the state estimates to determine the localization state.

17. The non-transitory, computer-readable medium of claim 15 wherein the operations further comprise outputting a graphical representation of the localization state to an operator, the graphical representation including a first visual indicator representing the estimated location and a second visual indicator representing the uncertainty parameter.

18. The non-transitory, computer-readable medium of claim 17 wherein the first and second visual indicators are displayed together with the 3D model of the anatomic region.

19. The non-transitory, computer-readable medium of claim 15 wherein the operations further comprise:

detecting that the uncertainty parameter is greater than a specified threshold;

outputting instructions to an operator to obtain additional data of the anatomic region; and updating the localization state using the additional data.

20. The system of claim 1, wherein determining the plurality of image capture locations includes determining a quantity of or an offset between the plurality of image capture locations based on a size of the anatomic region.

* * * * *